United States Patent
Vuskovic et al.

(10) Patent No.: US 8,298,773 B2
(45) Date of Patent: Oct. 30, 2012

(54) METHODS, ASSAYS AND KITS FOR CANCER DIAGNOSIS AND SCREENING UTILIZING GLYCAN-BINDING AND GLYCAN EPITOPES

(76) Inventors: Marko Vuskovic, Bonsall, CA (US); Margaret Huflejt, La Jolla, CA (US)

( * ) Notice: Subject to any disclaimer, the term of this patent is extended or adjusted under 35 U.S.C. 154(b) by 422 days.

(21) Appl. No.: 12/387,457

(22) Filed: May 1, 2009

(65) Prior Publication Data

US 2010/0075344 A1  Mar. 25, 2010

Related U.S. Application Data

(60) Provisional application No. 61/126,242, filed on May 2, 2008.

(51) Int. Cl.
*G01N 33/53* (2006.01)
*G01N 33/574* (2006.01)

(52) U.S. Cl. .................. 435/7.1; 435/7.21; 435/7.23

(58) Field of Classification Search .................. None
See application file for complete search history.

(56) References Cited

PUBLICATIONS

Boyd (The Basic Science of Oncology, 1992, McGraw-Hill, Inc., p. 379).*
Stites et al (Medical Immunology, 9th Ed, Appleton and Lange, 1997, p. 250-251).*
Tockman et al (Cancer Res., 1992, 52:2711s-2718s).*
Pritzker (Clinical Chemistry, 2002, 48:1147-1150).*
Von Gunten et al. (J. Allergy Clin. Immunol. 2009, pp. 1268-1276).*

* cited by examiner

*Primary Examiner* — Peter J Reddig
(74) *Attorney, Agent, or Firm* — Klauber & Jackson LLC

(57) ABSTRACT

The invention relates to the diagnosis, monitoring, prognosis, and/or prediction of cancer utilizing the detection or measurement of glycan-protein interactions, particularly glycan-antibody interactions. The invention relates to carbohydrate-containing molecules that are utilized in bioanalytical systems, methods and kits for detecting neoplasia and methods related thereto and based thereon. In an exemplary embodiment glycans or glycopolymers are carried in an array, on beads or in a microfluidic system for diagnostic screening for risk of neoplasia, the existence of neoplasia in a patient, or for treatment monitoring. In such an embodiment, the bioanalytic system identifies binding interactions between molecules in a patient test sample (e.g., glycan compositions) and the glycans or glycopolymers. The glycan-binding compositions may be used to generate an immune response against cancer cell epitopes. Alternatively, antibody therapeutics can be developed that are useful for binding to glycan compositions on a cell surface.

2 Claims, 2 Drawing Sheets

METHODS, ASSAYS AND KITS FOR CANCER DIAGNOSIS AND SCREENING UTILIZING GLYCAN-BINDING AND GLYCAN EPITOPES

CROSS REFERENCE TO RELATED APPLICATIONS

The present application is a non-provisional application claiming the priority of copending provisional application Ser. No. 61/126,242, filed May 2, 2008. Applicants claim the benefits of this application under 35 U.S.C. §119 (e).

FIELD OF THE INVENTION

The invention relates to the diagnosis, monitoring, prognosis, and/or prediction of cancer utilizing the detection or measurement of glycan-protein interactions, particularly glycan-antibody interactions. The invention relates to carbohydrate-containing molecules that are utilized in bioanalytical systems, methods and kits for detecting neoplasia and methods related thereto and based thereon. In one embodiment, the methods and systems of the invention identify binding interactions between molecules (glycan-binding compositions) in a patient test sample and the glycans or glycopolymers. The glycan-binding compositions may be used to generate an immune response against cancer cell epitopes. Antibodies binding to the cancer-associated glycans can be used as therapeutics.

BACKGROUND OF THE INVENTION

Cell surfaces carbohydrates, glycoproteins and glycolipids have multiple biological functions. Abnormalities in glycosylation are one of the basic mechanisms of malfunction (pathology) in living organisms, and particularly in cancers. Consequences of abnormal glycosylation are alteration of cell-cell recognition and signaling, activation of immune response, deregulation of cellular and tissue functions, and if persisting may result in malignant transformation. Malignant transformation and tumor progression can be correlated with specific changes in such complex surface carbohydrates, known as tumor-associated carbohydrate antigens (TACAs).

Glycans are typically the first and potentially the most important interface between cells and their environment. As vital constituents of all living systems, glycans are involved in recognition, adherence, motility and signaling processes. There are several reasons why glycans need to be studied: (1) all cells in living organisms, and viruses, are coated with diverse types of glycans; (2) glycosylation is a form of post- or co-translational modification occurring in all living organisms; and (3) altered glycosylation is an indication of an early and possibly critical point in development of human pathologies. Jun Hirabayashi, Oligosaccharide microarrays for glycomics; 2003, Trends in Biotechnology 21 (4): 141-143; Sen-Itiroh Hakomori, Tumor-associated carbohydrate antigens defining tumor malignancy: Basis for development of and cancer vaccines; in The Molecular Immunology of Complex Carbohydrates-2 (Albert M Wu, ed., Kluwer Academic/Plenum, 2001). These cell-identifying glycosylated molecules include glycoproteins and glycolipids and are specifically recognized by various glycan-recognition proteins. However, the enormous complexity of these interactions, and the lack of well-defined glycan libraries and analytical methods have been major obstacles in the development of glycomics.

The development of nucleotide and protein microarrays has revolutionized genomic, gene expression and proteomic research. The development of glycan microarrays has been slow, however, for a number of reasons. First, it has proven difficult to immobilize a library of chemically and structurally diverse glycans on arrays, beads or the like. Second, glycans are not readily amenable to analysis by many of the currently available molecular techniques (such as rapid sequencing and in vitro synthesis) that are routinely applied to nucleic acids and proteins. However, the use of glycan arrays could expedite screening procedures, making detection of cancer-related glycan epitopes simple and inexpensive.

Important to the successful and effective screening for glycan epitopes is glycan binding to a support that optimally exposes the three-dimensional glycan structure on the array or bead surface. Thus, new glyco-compounds and linking systems are being developed for advancing bioanalytic systems for early cancer detection and target discovery. A glycan array has been described in PCT/US2005/007370 filed Mar. 7, 2005 titled "High Throughput Glycan Microarrays" and U.S. Provisional Patent Application No. 60/629,666 filed Nov. 19, 2004 titled "Development of Blood Based Test Allowing Diagnosis of Neoplasia Status", both of which are incorporated herein by this reference in their entirety and made a part of this specification. New glyco-compounds and linking systems have been described in U.S. Provisional Patent Application No. 60/833,249 filed Jul. 26, 2006 titled "Bioanalytical Systems, Methods of Use and Business Methods" which is incorporated herein by this reference in its entirety and made a part of this specification.

Detection of diseases, such as cancers, at an early stage is beneficial for effective treatment. Monitoring of cancer and efficacy of cancer therapeutics is also vital to successful treatment and longer-term survival. Protein glycosylation is one of the most common post-translational modifications in mammals and humans. Although post-translational modification, and in particular, various glycans have been associated with the development and progression of cancers, there remains a need for specific and selective glycan markers of disease. The discovery of specific glycan markers, including combinations of markers, which provide for sensitive, selective and precise detection, monitoring, prognosis and/or prediction of cancer will advance the diagnosis and treatment of cancer.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

The present invention provides a series of glycan markers associated with and/or predictive of cancer. In particular sets of glycan markers are identified, binding proteins to which, particularly including antibodies, are found in altered relative amounts in patients who have cancer. These glycan markers were identified by analyses of antibodies from individuals with documented cancer. The altered presence or amounts of antibodies capable of binding to these glycan structures is associated with a particular type, form, or stage of cancer. These antiglycan autoantibodies are capable of binding to, or otherwise recognizing an aspect or epitope on the glycan markers. Assays detecting glycan binding may be used to assess or determine the presence or extent of cancer in a patient, and to monitor therapy, and assess residual disease. Such assays will augment existing diagnostic methodologies and allow identification and monitoring of patients. They will also facilitate the development of therapeutic agents directed at these or other cancers, while potentially highlighting new targets for such intervention. In addition, these glycan markers may have predictive value in other chronic/acute disease states in which contributing factors or resulting events in common with cancer occur including for instance, but not limited to pre-cancerous lesions, hyperproliferative diseases, or other diseases of the relevant organ, for example lung diseases in the instance of lung cancer markers.

The present invention provides methods and compositions for screening, diagnosis and treatment of cancer and neoplasia related conditions, and for screening and development of agents for treatment of such conditions. In particular methods, markers, kits, and compositions for diagnosis, monitoring, prediction, or prognosis of cancer are provided. Particular methods, markers, and kits for diagnosis, monitoring or lung cancer, breast cancer, and ovarian cancer are provided.

The invention provides methods for diagnosis or monitoring of cancer that comprise analyzing a test sample from a patient to detect the altered presence or level of glycan binding proteins, particularly of antiglycan antibodies, wherein said binding proteins bind, recognize, or associate with, one or more of the disease-associated glycan markers disclosed herein, or any combination thereof. These methods are also suitable, e.g., for clinical screening, prognosis, monitoring the results of therapy, for identifying patients most likely to respond to a particular therapeutic treatment, drug screening and development, and identification of new targets for drug treatment.

The invention provides kits that may be used in the above recited methods and that may comprise single or multiple preparations of glycans or oligosaccharides, together with other reagents, e.g., labels, substrates, if needed, and directions for use. The kits may be used for diagnosis of disease, or may be assays for the identification of new diagnostic and/or therapeutic agents, or to identify new targets for therapeutic agents.

An additional aspect of the invention provides methods of treating cancer or neoplasia, including in particular lung cancer, breast cancer, ovarian cancer, comprising administering to a subject a therapeutically effective amount of a modulator or agent or drug that modulates (e.g., upregulates or downregulates) the expression or activity (e.g. enzymatic or binding activity), or both, of one or more specific glycan marker or one or more antibody to said one or more glycan marker, in subjects having or suspected of having cancer, particularly including or selected from lung cancer, breast cancer, and ovarian cancer, and/or the conditions related thereto.

The invention provides methods of screening for agents that modulate (e.g., upregulate or downregulate) a characteristic of, e.g., the expression or the enzymatic or binding activity, or the chemical nature of one or more glycan marker of the invention, or an analog, a related oligosaccharide or glycan, or a glycan containing a core motif of said glycan marker.

In a general aspect, the invention provides a method of detecting or monitoring cancer in a patient comprising measuring at least one antiglycan binding profile of a test sample from said patient and comparing the measured profile with a profile of normal patient(s) or profile of a patient(s) with a family history of cancer, wherein a substantial difference in the test sample profile versus the normal or history of smoking profiles is indicative of cancer. In a such aspect, antiglycan binding to or against sulfated (sialo) lactosamines is measured or detected. The sulfated(sialo) lactosamines include, in general, any or one or more of a family of molecules having a general sulfated lactosamine core structure [3S and/or 6S]Galβ1-4GalcNAc[3S and/or 6S], including with or without sulfation, fucosylation and core extension at the reducing end. Altered binding to one or more members of such family of sulfated (sialo) lactosamines is associated with the presence of cancer in a patient. Exemplary such members and their association with cancer(s) are set out herein, including in the examples and as listed in Tables 5-13.

In a particular aspect, the invention provides a method of detecting or monitoring lung cancer in a patient comprising measuring at least one antiglycan binding profile of a test sample from said patient and comparing the measured profile with a profile of normal patient or profile of a patient with a history of smoking, wherein a substantial difference in the test sample profile versus the normal or history of smoking profiles is indicative of lung cancer.

In a particular such method, the measuring step comprises measuring at least two antiglycan binding profiles against at least two glycans selected from the group of glycans of Table 5. In a further method, the measuring step comprises measuring a combination of the antiglycan binding profiles against the group of glycans of Table 5. The measuring step in an additional method may comprise measuring at least two antiglycan a binding profiles against at least two glycans selected from the group of glycans of Tables 5 and 6. In a further method, the measuring step comprises measuring a combination of the antiglycan binding profiles against the group of glycans of Table 6.

The invention includes a method for diagnosing a patient for lung cancer or risk of lung cancer comprising obtaining a test sample from a patient and detecting the altered presence or amount of antiglycan autoantibodies against at least one cell surface glycan selected from the group listed in Table 5.

The invention provides a method for diagnosing a patient for lung cancer or risk of lung cancer comprising obtaining a test sample from a patient and detecting the presence of antiglycan autoantibodies against a combination of the glycans listed in Table 5. The invention includes a method for diagnosing a patient for lung cancer or risk of lung cancer comprising obtaining a test sample from a patient and detecting the altered presence or amount of antiglycan autoantibodies against a combination of the glycans listed in Table 6.

In one aspect of the above methods, adenocarcinoma of the lung is detected or diagnosed.

In a further particular aspect, the invention provides a method of detecting or monitoring breast cancer in a patient comprising measuring at least one antiglycan binding profile of a test sample from said patient and comparing the measured profile with a profile of normal patient or profile of a patient with a family history of breast cancer, wherein a substantial difference in the test sample profile versus the normal or history of smoking profiles is indicative of breast cancer.

A method is provided for detecting, diagnosing or monitoring breast cancer in a patient is provided herein comprising obtaining a test sample from a patient and detecting the altered presence or amount of antiglycan antibodies against at least one of the glycans listed in Table 7, or at least one of the glycans listed in Table 9.

A method for detecting, diagnosing or monitoring breast cancer in a patient is provided herein comprising obtaining a test sample from a patient and detecting the altered presence or amount of antiglycan antibodies against at least one of the glycans listed in Table 8 and 10. The method may comprise obtaining a test sample from a patient and detecting the presence of antiglycan antibodies against at least one of the glycans listed in Table 8, listed in Table 10, or listed in both Table 8 and 10.

A method for facilitating the diagnosis of DCIS in a patient is provided comprising obtaining a test sample from a patient and detecting the altered presence or amount of antiglycan autoantibodies against at least one of the glycans listed in Table 8.

A method for facilitating the diagnosis of IDC in a patient is provided comprising obtaining a test sample from a patient and detecting the presence of antiglycan autoantibodies against at least one of the glycans listed in Table 10.

In an additional particular aspect, the invention provides a method of detecting or monitoring ovarian cancer in a patient comprising measuring at least one antiglycan binding profile of a test sample from said patient and comparing the measured profile with a profile of normal patient or profile of a patient with a family history of ovarian cancer, wherein a substantial difference in the test sample profile versus the normal or history of smoking profiles is indicative of ovarian cancer.

A method for detecting, diagnosing or monitoring ovarian cancer in a patient may comprise obtaining a test sample from a patient and detecting the altered presence or amount of antiglycan autoantibodies against at least one of the glycans listed in Table 12.

In a further aspect, the invention provides a method for diagnosis or monitoring of cancer in a patient comprising:

screening a patient test sample for the presence of glycan-binding moieties against the glycans set out in one or more of Tables 5-13 to produce binding data;

collecting the binding data into a database;

using one or more bioinformatic algorithms to process the collected binding data for said patient versus binding data for one or more control patient or normal populations; and identifying altered presence or amounts of glycan-binding moieties in said patient and thereby diagnosing or monitoring cancer in said patient.

In an additional aspect of the invention, a method is provided for detecting or monitoring mesothelioma in a patient comprising measuring at least one antiglycan binding profile of a test sample from said patient and comparing the measured profile with a profile of normal patient or profile of a patient exposed to asbestos, wherein a substantial difference in the test sample profile versus the normal or asbestos exposed profiles is indicative of mesothelioma. In a particular such method, the measuring step comprises measuring one or more antiglycan binding profiles against one or more glycans selected from the group of glycans of Table 15.

The invention additionally provides a kit for diagnosing or monitoring cancer in an individual wherein the antiglycan binding profile of a test sample from said individual is determined and comparing the measured profile with a profile of normal patient or profile of a patient with a family history of cancer, wherein said kit comprises an array of glycan molecules selected from the glycans set out in Tables 6, 8, 10 and 12. The kit may comprise an array wherein the array comprises at least one glycan selected from each of Tables 6, 8, 10 and 12.

In an aspect, the invention includes such a kit for diagnosing or monitoring lung cancer, wherein said kit comprises one or more glycan molecules selected from the glycans set out in Table 6. In one aspect, the said lung cancer kit comprises an array of glycan molecules selected from the glycans set out in Table 6. In an aspect, the invention includes such a kit for diagnosing or monitoring breast cancer, wherein said kit comprises one or more glycan molecules selected from the glycans set out in Table 8, and/or one or more glycan molecules selected from the glycans in Table 10. In one aspect, the said breast cancer kit comprises an array of glycan molecules selected from the glycans set out in Table 8. In a further aspect, the said breast cancer kit comprises an array of glycan molecules selected from the glycans set out in Table 10. In an aspect, the invention includes such a kit for diagnosing or monitoring ovarian cancer, wherein said kit comprises one or more glycan molecules selected from the glycans set out in Table 12, and/or one or more glycan molecules selected from the glycans in Table 13. In one aspect, the said breast cancer kit comprises an array of glycan molecules selected from the glycans set out in Table 12.

The invention provides a kit for diagnosing or monitoring mesothelioma in an individual wherein the antiglycan binding profile of a test sample from said individual is determined and comparing the measured profile with a profile of normal patient or profile of a patient exposed to asbestos, wherein said kit comprises one or more glycan molecules selected from the glycans set out in Table 15.

Other objects and advantages will become apparent to those skilled in the art from a review of the following description which proceeds with reference to the following illustrative drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
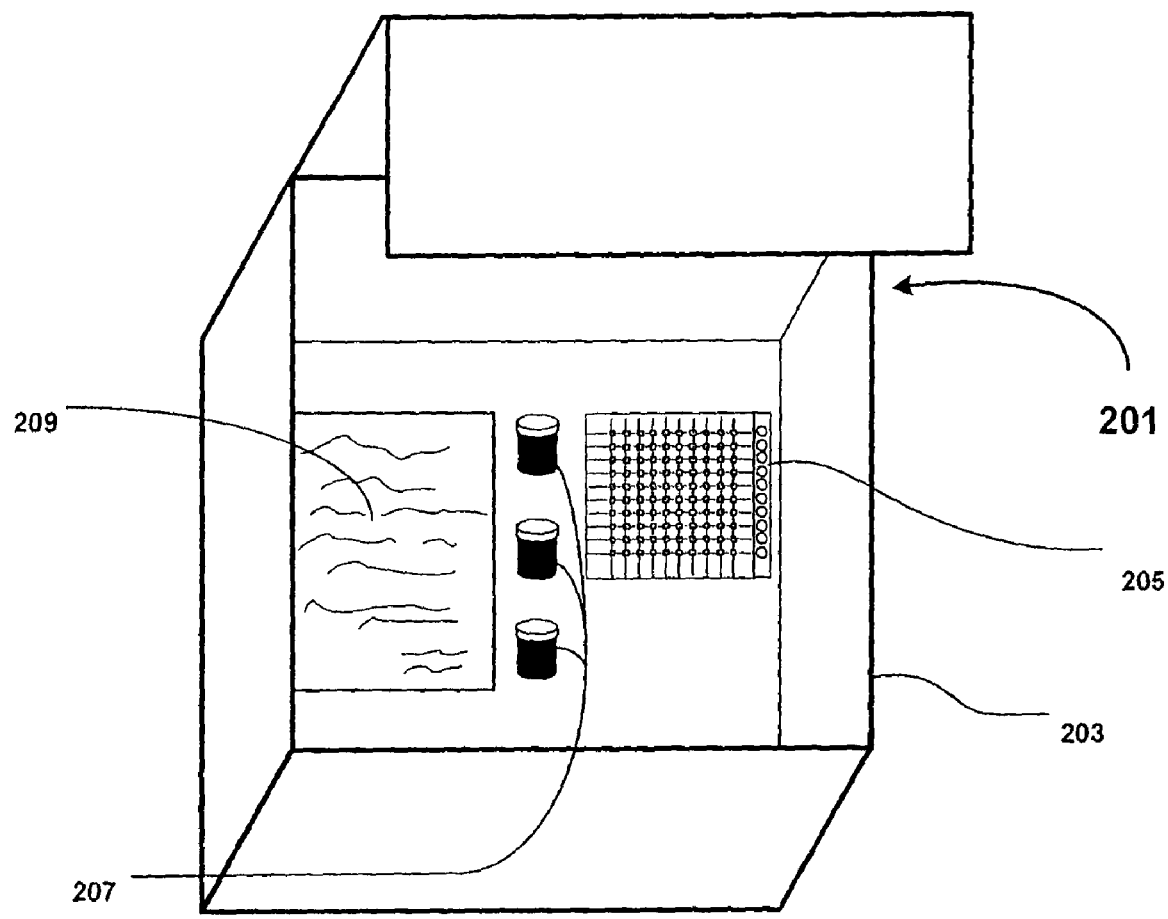
FIG. 1 is a block diagram showing a representative example of a kit.

As used in the specification, "a" or "an" means one or more. As used in the claim(s), when used in conjunction with the word "comprising", the words "a" or "an" mean one or more. As used herein, "another" means as least a second or more.

Glycomics (also referred to as glycobiology) is a discipline of biology concerned with the structure and function of mono- and oligosaccharides. Glycomics is the foundation upon which various embodiments of the inventions described herein are based. Certain business methods disclosed herein are useful for identifying marketing or commercializing glycomics-related diagnostic, therapeutic and/or imaging probe products. Glycomics-related products of the invention include but are not limited to products for producing oligosaccharides, reactive antibody products, and monoclonal antibody cocktail products. Methods of conducting glycomics-related cancer trials are also disclosed.

Detection/Treatment/Prevention of Early Stage Diseases and/or Neoplasia

Libraries and arrays of glycans can be embodiments of the implementations of the methods disclosed herein. The libraries and arrays of glycans can find uses directed to detecting, treating and/or preventing a variety of early stage diseases and/or neoplasias. In one embodiment, the neoplasia being detected is ovarian cancer. According to the invention, ovarian cancer patients, even early stage ovarian cancer patients, have circulating antibodies that react with cancer-related epitopes and many of those epitopes are glycans. The detection of such antibodies in a patient is indicative of ovarian cancer, or the propensity to develop ovarian cancer. Thus, even non-symptomatic women can be quickly tested using the libraries, arrays and methods of the invention to ascertain whether they have no risk or a low risk or a high risk of developing ovarian cancer. In some embodiments, the presence of such antibodies is indicative of the presence of established ovarian cancer and can provide information on the prognosis of such an established disease, for example, whether the disease is in remission or is becoming more aggressive. Patients with familial history of ovarian cancer, and hence a heightened risk of developing the disease, can be tested regularly to monitor their propensity for disease.

Another aspect of the invention is a composition of glycans that can be used for treating or preventing ovarian cancer. The compositions include glycans used to elicit protective immune response in patients with a high risk of developing ovarian malignancies. The compositions can also be used to enhance the immune response of patients that have ovarian cancer. The compositions can also be used to prepare isolated antibody preparations useful for passive immunization of patients who have developed or may develop ovarian cancer.

The following abbreviations may be used herein: $\alpha_1$-AGP means alpha-acid glycoprotein; AF488 means AlexaFluour-488; CFG means Consortium for Functional Glycomics; Con A means Concanavalin A; CVN means cyanovirin-N; DC-SIGN means dendritic cell-specific ICAM-grabbing nonintegrin; ECA means *erythrina cristagalli*; ELISA means enzyme-linked immunosorbent assay; FITC means Fluorescinisothiocyanate; GBP means Glycan Binding Protein; HIV means human immunodeficiency virus; HA means influenza hemagglutinin; NHS means N-hydroxysuccinimide; PBS means phosphate buffered saline; SDS means sodium dodecyl sulfate; SEM means standard error of mean; and Siglec means sialic acid immunoglobulin superfamily lectins.

A "defined glycan probe location" as used herein is a predefined region of a solid support to which a density of glycan molecules, all having similar glycan structures, is attached. The terms "glycan region," or "selected region", or simply "region" are used interchangeably herein for the term defined glycan probe location. The defined glycan probe location may have any convenient shape, for example, circular, rectangular, elliptical, wedge-shaped, and the like. In some embodiments, a defined glycan probe location and, therefore, the area upon which each distinct glycan type or a distinct group of structurally related glycans is attached is smaller than about 1 cm², or less than 1 mm², or less than 0.5 mm². In some embodiments the glycan probe locations have an area less than about 10,000 µm² or less than 100 µm². In one embodiment, the glycan molecules attached within each defined glycan probe location are substantially identical. Additionally, multiple copies of each glycan type are present within each defined glycan probe location. The number of copies of each glycan types within each defined glycan probe location can be in the thousands to the millions.

As used herein, the arrays of the invention have defined glycan probe locations, each with "one type of glycan molecule." The "one type of glycan molecule" employed can be a group of substantially structurally identical glycan molecules or a group of structurally similar glycan molecules. There is no need for every glycan molecule within a defined glycan probe location to have an identical structure. In some embodiments, the glycans within a single defined glycan probe location are structural isomers, have variable numbers of sugar units or are branched in somewhat different ways. However, in general, the glycans within a defined glycan probe location have substantially the same type of sugar units and/or approximately the same proportion of each type of sugar unit. The types of substituents on the sugar units of the glycans within a defined glycan probe location are also substantially the same.

The term "glycan", "glycan marker", "disease-associated glycan" in each and any such instance, including the particular disease associated glycan markers as set out in Tables 5-13 herein shall include glycans of similar or related structure. Thus the term glycan shall be interpreted to encompass and include the specific glycan markers as set out herein, or an analog, a related oligosaccharide or glycan, or a glycan containing, for instance a similar or a core motif of said glycan marker. A marker of use in the present invention and methods may include a natural or synthetic and/or related glycan. Thus, glycans may be modified to generate analogs or derivatives, which can be confirmed or determined to be similarly bound by the relevant disease-associated antiglycan antibodies. It is well within the skill and knowledge of the skilled artisan to make and test any such analogs or derivatives. Analogs or derivatives with like structure or core similar structures and the same or similar binding profiles may be used in the methods, kits and systems of the invention.

As used herein a "patient" is a mammal. Such mammals include domesticated animals, animals used in experiments, zoo animals and the like. For example, the patient can be a dog, cat, monkey, horse, rat, mouse, rabbit, goat, ape or human mammal. In many embodiments, the patient is a human.

Some of the structural elements of the glycans described herein are referenced in abbreviated form. Many of the abbreviations used are provided in the following table. Moreover the glycans of the invention may have any of the sugar units, monosaccharides or core structures provided in Table 1.

TABLE 1

| Trivial Name | Monosaccharide/Core | Code |
| --- | --- | --- |
| D-Glcp | D-Glucopyranose | G |
| D-Galp | D-Galactopyranose | A |
| D-GlcpNAc | N-Acetylglucopyranose | GN |
| D-GlcpN | D-Glucosamine | GQ |
| D-GalpNAc | N-Acetylgalactopyranose | AN |
| D-GalpN | D-Galacosamine | AQ |
| D-Manp | D-Mannopyranose | M |
| D-ManpNAc | D-NJ-Acetylmannopyranose | MN |
| D-Neup5Ac | N-Acetylneuraminic acid | NN |
| D-Neu5G | D-N-Glycolylneuraminic acid | NJ |
| D-Neup | Neuraminic acid | N |
| KDN* | 2-Keto-3-deoxynananic acid | K |
| Kdo | 3-deoxy-D-manno-2 octulopyranosylono | W |
| D-GalpA | D-Galactoronic acid | L |
| D-Idop | D-Iodoronic acid | I |
| L-Rhap | L-Rhamnopyranose | H |
| L-Fucp | L-Fucopyranose | F |
| D-Xylp | D-Xylopyranose | X |
| D-Ribp | D-Ribopyranose | B |
| L-Araf | L-Arabinofuranose | R |
| D-GlcpA | D-Glucoronic acid | U |
| D-Allp | D-Allopyranose | O |
| D-Apip | D-Apiopyranose | P |
| D-Tagp | D-Tagopyranose | T |
| D-Abep | D-Abequopyranose | Q |
| D-Xulp | D-Xylulopyranose | D |
| D-Fruf | D-Fructofuranose | E |

*Another description of KDN is: 3-deoxy-D-glycero-K-galacto-nonulosonic acid

The sugar units or other saccharide structures present in the glycans of the invention can be chemically modified in a variety of ways. A listing of some of the types of modifications and substituents that the sugar units in the glycans of the invention can possess, along with the abbreviations for these modifications/substituents are listed below in Table 2.

TABLE 2

| Modification type | Symbol |
| --- | --- |
| Acid | A |
| deacetylated N-Acetyl (amine) | Q |
| Deoxy | Y |
| Ethyl | ET |
| Hydroxyl | OH |
| Inositol | IN |
| Methyl | ME |
| N-Acetyl | N |
| N-Glycolyl | J |
| N-Methylcarbamoyl | ECO |
| N-Sulfate | QS |
| O-Acetyl | T |
| Octyl | EH |
| Pentyl | EE |
| Phosphate | P |
| Phosphocholine | PC |
| Phosphoethanolamine (2-aminoethylphosphate) | PE |
| Pyrovat acetal | PYR* |
| Sulfate | S |

*When written on position 3, it means 3, 4, when to 4 it means 4, 6.

Glycans

The invention provides libraries of glycans that are useful for detecting and preventing cancer, including but not limited to lung cancer, breast cancer, and ovarian cancer. These glycan libraries can include numerous different types of carbohydrates and oligosaccharides. However, at a minimum, the glycan libraries for detecting cancer include N-acetyllactosamine-containing glycans. In general, the major structural attributes and composition of the separate glycans within the libraries have been identified. In some embodiments, the libraries consist of separate, substantially pure pools of glycans, carbohydrates and/or oligosaccharides. Further description of the types of glycans useful in the practice of the invention is provided in U.S. Provisional Ser. No. 60/550,667, filed Mar. 5, 2004, U.S. Provisional Ser. No. 60/558,598, filed Mar. 31, 2004, PCT Application Ser. No. PCT/US2005/04273 and U.S. Provisional Ser. No. 60/558,598, filed Mar. 31, 2004, the contents of which are incorporated herein by reference.

The glycans of the invention include straight chain and branched oligosaccharides as well as naturally occurring and synthetic glycans. For example, the glycan can be a glycoaminoacid, a glycopeptide, a glycolipid, a glycoaminoglycan (GAG), a glycoprotein, a whole cell, a cellular component, a glycoconjugate, a glycomimetic, a glycophospholipid anchor (GPI), glycosyl phosphatidylinositol (GPI)-linked glycoconjugates, bacterial lipopolysaccharides and endotoxins. The glycans can also include N-glycans, O-glycans, glycolipids and glycoproteins.

The glycans of the invention include 2 or more sugar units. Any type of sugar unit can be present in the glycans of the invention, including, for example, allose, altrose, arabinose, glucose, galactose, gulose, fucose, fructose, idose, lyxose, mannose, ribose, talose, xylose, or other sugar units. The tables provided herein list other examples of sugar units that can be used in the glycans of the invention. Such sugar units can have a variety of modifications and substituents. Some examples of the types of modifications and substituents contemplated are provided in the tables herein. For example, sugar units can have a variety of substituents in place of the hydroxy (—OH), carboxylate (—COO⁻), and methylenehydroxy (—CH$_2$—OH) substituents. Thus, lower alkyl moieties can replace any of the hydrogen atoms from the hydroxy (—OH), carboxylic acid (—COOH) and methylenehydroxy (—CH$_2$—OH) substituents of the sugar units in the glycans of the invention. For example, amino acetyl (—NH—CO—CH$_3$) can replace any of the hydroxy or hydrogen atoms from the hydroxy (—OH), carboxylic acid (—COOH) and methylenehydroxy (—CH$_2$—OH) substituents of the sugar units in the glycans of the invention. N-acetylneuraminic acid can replace any of the hydrogen atoms from the hydroxy (—OH), carboxylic acid (—COOH) and methylenehydroxy (—CH$_2$—OH) substituents of the sugar units in the glycans of the invention. Sialic acid can replace any of the hydrogen atoms from the hydroxy (—OH), carboxylic acid (—COOH) and methylenehydroxy (—CH$_2$—OH) substituents of the sugar units in the glycans of the invention. Amino or lower alkyl amino groups can replace any of the OH groups on the hydroxy (—OH), carboxylic acid (—COOH) and methylenehydroxy (—CH$_2$—OH) substituents of the sugar units in the glycans of the invention. Sulfate (—SO$_4^-$) or phosphate (—PO$_4^-$) can replace any of the OH groups on the hydroxy (—OH), carboxylic acid (—COOH) and methylenehydroxy (—CH$_2$—OH) substituents of the sugar units in the glycans of the invention. Hence, substituents that can be present instead of, or in addition to, the substituents typically present on the sugar units include N-acetyl, N-acetylneuraminic acid, oxy (=O), sialic acid, sulfate (—SO$_4^-$), phosphate (—PO$_4^-$), lower alkoxy, lower alkanoyloxy, lower acyl, and/or lower alkanoylaminoalkyl.

The following definitions are used, unless otherwise described: Alkyl, alkoxy, alkenyl, alkynyl, etc. denote both straight and branched groups; but reference to an individual radical such as "propyl" embraces only the straight chain radical, when a branched chain isomer such as "isopropyl" has been specifically referred to. Halo is fluoro, chloro, bromo, or iodo.

Specifically, lower alkyl refers to (C$_1$-C$_6$)alkyl, which can be methyl, ethyl, propyl, isopropyl, butyl, iso-butyl, sec-butyl, pentyl, 3-pentyl, or hexyl; (C$_3$-C$_6$)cycloalkyl can be cyclopropyl, cyclobutyl, cyclopentyl, or cyclohexyl; (C$_3$-C$_6$)cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$-C$_6$)alkoxy can be methoxy, ethoxy, propoxy, isopropoxy, butoxy, iso-butoxy, sec-butoxy, pentoxy, 3-pentoxy, or hexyloxy.

It will be appreciated by those skilled in the art that the glycans of the invention having one or more chiral centers may exist in and be isolated in optically active and racemic forms. Some compounds may exhibit polymorphism. It is to be understood that the present invention encompasses any racemic, optically-active, polymorphic, or stereoisomeric form, or mixtures thereof, of a glycan of the invention, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific and preferred values listed below for substituents and ranges, are for illustration only; they do not exclude other defined values or other values within defined ranges or for the substituents.

The libraries of the invention are particularly useful because diverse glycan structures are difficult to make and substantially pure solutions of a single glycan type are hard to generate. For example, because the sugar units typically present in glycans have several hydroxyl (—OH) groups and each of those hydroxyl groups is substantially of equal chemical reactivity, manipulation of a single selected hydroxyl group is difficult. Blocking one hydroxyl group and leaving one free is not trivial and requires a carefully designed series of reactions to obtain the desired regioselectivity and stereoselectivity. Moreover, the number of manipulations required increases with the size of the oligosaccharide. Hence, while synthesis of a disaccharide may require 5 to 12 steps, as many as 40 chemical steps can be involved in synthesis of a typical tetrasaccharide. Thus, the chemical synthesis of oligosaccharides is highly complex The glycans of the invention can be obtained by a variety of procedures. For example, some of the chemical approaches developed to prepare N-acetyllactosamines by glycosylation between derivatives of galactose and N-acetylglucosamine are described in Aly, M. R. E.; Ibrahim, E.-S. I.; El-Ashry, E.-S. H. E. and Schmidt, R. R., *Carbohydr. Res.* 1999, 316, 121-132; Ding, Y.; Fukuda, M. and Hindsgaul, O., *Bioorg. Med Chem. Lett.* 1998, 8, 1903-1908; Kretzschmar, G. and Stahl, W., *Tetrahedr.* 1998, 54, 6341-6358. These procedures can be used to make the glycans of the present libraries, but because there are numerous protection-deprotection steps involved in such chemical syntheses, the amounts of products obtained in these methods can be low.

One way to avoid protection-deprotection steps typically required during glycan synthesis is to mimic nature's way of synthesizing oligosaccharides by using regiospecific and stereospecific enzymes, called glycosyltransferases, for coupling reactions between the monosaccharides. These enzymes catalyze the transfer of a monosaccharide from a glycosyl donor (usually a sugar nucleotide) to a glycosyl acceptor with high efficiency. Most enzymes operate at room temperature in aqueous solutions (pH 6-8), which makes it possible to combine several enzymes in one pot for multi-step reactions. The high regioselectivity, stereoselectivity and catalytic efficiency make enzymes especially useful for synthesis of some oligosaccharides and glycoconjugates. See Koeller, K. M. and Wong, C.-H., *Nature* 2001, 409, 232-240; Wymer, N. and Toone, E. J., *Curr. Opin. Chem. Biol.* 2000, 4, 110-119; Gijsen, H. J. M.; Qiao, L.; Fitz, W. and Wong, C.-H., *Chem. Rev.* 1996, 96, 443-473.

Recent advances in isolating and cloning glycosyltransferases from mammalian and non-mammalian sources such as bacteria also can facilitate production of various oligosaccharides. DeAngelis, P. L., *Glycobiol.* 2002, 12, 9R-16R; Endo, T. and Koizumi, S., *Curr. Opin. Struct. Biol.* 2000, 10, 536-541; Johnson, K. F., *Glycoconj. J.* 1999, 16, 141-146. In general, bacterial glycosyltransferases are more relaxed regarding donor and acceptor specificities than mammalian glycosyltransferases. Moreover, bacterial enzymes are well expressed in bacterial expression systems such as *E. coli* that can easily be scaled up for over expression of the enzymes. Bacterial expression systems lack the post-translational modification machinery that is required for correct folding and activity of the mammalian enzymes whereas the enzymes from the bacterial sources are compatible with this system. Thus, in many embodiments, bacterial enzymes are used as synthetic tools for generating glycans, rather than enzymes from the mammalian sources.

For example, the repeating Galβ(1-4)G1cNAc-unit can be enzymatically synthesized by the concerted action of β4-galactosyltransferase (β4GalT) and β3-N-acetyllactosamninyltransferase (β3GlcNAcT). Fukuda, M., *Biochim. Biophys. Acta.* 1984, 780:2, 119-150; Van den Eijnden, D. H.; Koenderman, A. H. L. and Schiphorst, W. E. C. M., *J. Biol. Chem.* 1988, 263, 12461-12471. The inventors have previously cloned and characterized the bacterial *N. meningitides* enzymes β4GalT-GalE and β3GlcNAcT and demonstrated their utility in preparative synthesis of various galactosides. Blixt, O.; Brown, J.; Schur, M.; Wakarchuk, W. and Paulson, J. C., *J. Org. Chem.* 2001, 66, 2442-2448; Blixt, O.; van Die, I.; Norberg, T. and van den Eijnden, D. H., Glycobiol. 1999, 9, 1061-1071. β4GalT-GalE is a fusion protein constructed from β4GalT and the uridine-5'-diphospho-galactose-4'-epimerase (GalE) for in situ conversion of inexpensive UDP-glucose to UDP-galactose providing a cost efficient strategy.

In most cases, the structures of the glycans used in the compositions, libraries, arrays, methods, and kits of the invention are described herein. However, in some cases a source of the glycan, rather than the precise structure of the glycan is given. Hence, a glycan from any available natural source can be used in the arrays and libraries of the invention. For example, known glycoproteins are a useful source of glycans. The glycans from such glycoproteins can be isolated using available procedures or, for example, procedures provided herein. Such glycan preparations can then be used in the compositions, libraries and arrays of the invention.

Examples of glycans provided in the libraries and on the arrays of the invention are provided in Table 3. Abbreviated names as well as complete names are provided.

TABLE 3

| Glycan |
|---|
| AGP α-acid glycoprotein |
| AGPAα-acid glycoprotein glycoformA |
| AGPBα-acid glycoprotein glycoformB |
| Ceruloplasmine |
| Fibrinogen |
| Transferrin |
| (Ab4[Fa3]GNb)2#sp1 LeX |
| (Ab4[Fa3]GNb)3#sp1 LeX |
| (Ab4GNb)3#sp1 Tri-LacNAc |
| [3OSO3]Ab#sp2 3SuGal |
| [3OSO3]Ab3ANa#sp2 3'SuGalβ3GalNAc |
| [3OSO3]Ab3GNb#sp2 3'SuGalβ3GalNAc |
| [3OSO3]Ab4[6OSO3]Gb#sp1 3'6DiSuLac |
| [3OSO3]Ab4[6OSO3]Gb#sp2 3'6DiSuLac |
| [3OSO3]Ab4Gb#sp2 3'SuLac |
| [3OSO3]Ab4GNb#sp2 3'SuLacNAc |
| [4OSO3]Ab4GNb#sp2 4'SuLacNAc |
| [6OPO3]Ma#sp2 6PMan |
| [6OSO3]Ab4[6OSO3]Gb#sp2 6'6DiSuLac |
| [6OSO3]Ab4Gb#sp1 6'SuLac |
| [6OSO3]Ab4Gb#sp2 6'SuLac |
| [6OSO3]GNb#sp2 6SuGlcNAc |
| [GNb3[GNb6]GNb4]Ana#sp2 |
| [NNa3Ab]2GNb#sp2 (Sia)2GlcNAc |
| 3OSO3Ab3[Fa4]GNb#sp2 3'SuLe a |
| 3OSO3Ab4[Fa3]GNb#sp2 3'SuLe X |
| 9NAcNNa#sp2 9NAc-Neu5Ac |
| 9NAcNNa6Ab4GNb#sp2 9NAc-Neu5Ac2,6LacNAc |
| Aa#sp2 Galα |
| Aa2Ab#sp2 Galα2Gal |
| Aa3[Aa4]Ab4GNb#sp2 Galα3[Galα4]LacNAc |
| Aa3[Fa2]Ab#sp2 Galα3[Fuc]Galβ |
| Aa3Ab#sp2 Galα3Gal |
| Aa3Ab4[Fa3]GN#sp2 Galα3Le X |
| Aa3Ab4Gb#sp1 Galα3Lac |
| Aa3Ab4GN#sp2 Galα3LacNAc |
| Aa3Ab4GNb#sp2 Galα3LacNAc |
| Aa3ANa#sp2 Galα3GalNac |
| Aa3ANb#sp2 Galα3GalNAc |
| Aa4[Fa2]Ab4GNb#sp2 Galα4[Fucα2]LacNAc |
| Aa4Ab4Gb#sp1 Galα4Lac |
| Aa4Ab4GNb#sp1 Galα4LacNAc |
| Aa4Ab4GNb#sp2 Galα4LacNAc |
| Aa4GNb#sp2 Galα4GlcNAc |

TABLE 3-continued

| Glycan |
|---|
| Aa6Gb#sp2 Galα6Gal |
| Ab#sp2 Gal |
| Ab[NNa6]ANa#sp2 6Sialyl-T |
| Ab2Ab#sp2 Galβ2Gal |
| Ab3[Ab4GNb6]ANa#sp2 6LacNAc-Core2 |
| Ab3[Fa4]GNb#sp1 Le a |
| Ab3[Fa4]GNb#sp2 Le a |
| Ab3[GNb6]ANa#sp2 Core-2 |
| Ab3[NNa6]GNb4Ab4Gb#sp4 LSTc |
| Ab3[NNb6]ANa#sp2 β6Sialyl-T |
| Ab3Ab#sp2 Galβ ® Gal |
| Ab3ANa#sp2 Gal ® 3GalNAcα |
| Ab3ANb#sp2 Gal ® 3GalNAcβ |
| Ab3ANb4[NNa3]Ab4Gb#sp1 GM1 |
| Ab3ANb4Ab4Gb#sp2 a-sialo-GM1 |
| Ab3GNb#sp1 LeC |
| Ab3GNb#sp2 LeC |
| Ab3GNb3Ab4Gb4b#sp4 LNT |
| Ab4[6OSO3]Gb#sp16SuLac |
| Ab4[6OSO3]Gb#sp2 6SuLac |
| Ab4[Fa3]GNb#sp1 LeX |
| Ab4[Fa3]GNb#sp2 LeX |
| Ab4ANa3[Fa2]Ab4GNb#sp2 |
| Ab4Gb#sp1 Lac |
| Ab4Gb#sp2 Lac |
| Ab4GNb#sp1 LacNAc |
| Ab4GNb#sp2 LacNAc |
| Ab4GNb3[Ab4GNb6]ANa#sp2 (LacNAc)2-Core2 |
| Ab4GNb3Ab4[Fa3]GNb3Ab4[Fa3]GNb#sp1 LacNAc-LeX-LeX |
| Ab4GNb3Ab4Gb#sp1 LNnT |
| Ab4GNb3Ab4Gb#sp2 LNnT |
| Ab4GNb3Ab4GNb#sp1 LacNAc-LacNAc |
| Ab4GNb3ANa#sp2a 3LacANcα-Core-2 |
| Ab4GNb3ANa#sp2b 3LacANcβ-Core-2 |
| Ab4GNb6ANa#sp2 6LacANcα-Core-2 |
| ANa#sp2 Tn |
| ANa3[Fa2]Ab#sp2 A-tri |
| ANa3Ab#sp2 GalNAcα3Gal |
| ANa3Ab4GNb#sp2 GalNAcα3LacNAc |
| ANa3ANb#sp2 GalNAcα3GalNAc |
| ANa4[Fa2]Ab4GNb#sp2 GalNAcα4[Fucα2]LacNAc |
| ANb#sp2 GalNAcβ |
| ANb3[Fa2]Ab#sp2 GalNAcβ[Fucα2]Gal |
| ANb3Ana#sp2 GAlNAcβ3GalNAc |
| ANb4GNb#sp1 LacDiNAc |
| ANb4GNb#sp2 LacDiNAc |
| Fa#sp2 Fuc |
| Fa#sp3 Fuc |
| Fa2Ab#sp2 Fucα2Gal |
| Fa2Ab3[Fa4]GNb#sp2 Le b |
| Fa2Ab3Ana#sp2 H-type 3 |
| Fa2Ab3Anb3Aa#sp3 H-type3β3Gal |
| Fa2Ab3Anb3Aa4Ab4G#sp3 Globo-H |
| Fa2Ab3ANb4[NNa3]Ab4Gb#sp1 Fucosyl-GM1 |
| Fa2Ab3GNb#sp1 H-type 1 |
| Fa2Ab3GNb#sp2 H type 1 |
| Fa2Ab4[Fa3]GNb#sp1 Le Y |
| Fa2Ab4[Fa3]GNb#sp2 LeY |
| Fa2Ab4Gb#sp1 2'FLac |
| Fa2Ab4GNb#sp1 H-type 2 |
| Fa2Ab4GNb#sp2 H-type 2 |
| Fa2Ab4GNb3Ab4GNb#sp1 H-type-2-LacNAc |
| Fa2Ab4GNb3Ab4GNb3Ab4GNb#sp1 H-type2-LacNAc-LacNAc |
| Fa2GNb#sp2 Fucα2GlcNAc |
| Fa3GNb#sp2 Fucα3GlcNAc |
| Fb3GNb#sp2 Fucβ3GLcNAc |
| Fa2Ab3ANb4[NNa3]Ab4Gb#sp3 Fucosyl-GM1 |
| Ga#sp2 Galα |
| Ga4Gb#sp2 Galα4Gal |
| Gb#sp2 Galβ |
| Gb4Gb#sp2 Galβ4Gal |
| Gb6Gb#sp2 Galβ6Gal |
| GNb#sp1 GlcNAc |
| GNb#sp2 GlcNAc |
| GNb2Ab3ANa#sp2 GlcNAcβ2-Core-1 |
| GNb3[GNb6]ANa#sp2 |
| GlcNAcβ3[GlcNAcβ6GalNAc |
| GNb3Ab#sp2 GlcNAcβ3Gal |
| GNb3Ab3ANa#sp2 GlcNAcβ3-Core1 |
| GNb3Ab4Gb#sp1 LNT-2 |
| GNb3Ab4GNb#sp1 GlcNAcβ3LacNAc |
| GNb4[GNb6]ANa#sp2 |
| GlcNAcβ4[GlcNAcβ6]GalNAc |
| GNb4GNb4GNb4b#sp2 Chitotriose |
| GNb4MDPLys |
| GNb6ANs#sp2 GlcANcβ6GalNAc |
| G-ol-amine glucitolamine |
| GUa#sp2 Glucurinic acidα |
| GUb#sp2 Glucuronic acidβ |
| Ka3Ab3GNb#sp1 KDNα2,3-type1 |
| Ka3Ab4GNb#sp1 KDBα2,3-LacNAc |
| Ma#sp2 Mannose α |
| Ma2Ma2MA3Ma#sp3 |
| Ma2Ma3[Ma2Ma6]Ma#sp3 |
| Ma2Ma3Ma#sp3 |
| Ma3[Ma2Ma2Ma6]Ma#sp3 |
| Ma3[Ma6]Ma#sp3 Man-3 |
| Man-5#aa Man5-aminoacid |
| Man5-9 pool Man5-9-aminoacid |
| Man-6#aa Man6-aminoacid |
| Man-7#aa Man7-aminoacid |
| Man-8#aa Man8-aminoacid |
| Man-9#aa Man9-aminoacid |
| Na8Na#sp2 Neu5Acα2,8Neu5Ac |
| Na8Na8Na#sp2 Neu5Acα2,8Neu5Acα2,5Neu5Ac |
| NJa#sp2 Neu5Gc |
| NJa3Ab3[Fa4]GNb#sp1 Neu5GcLe a |
| NJa3Ab3GbN#sp1 Neu5Gc-type1 |
| NJa3Ab4[Fa3]GNb#sp1 Neu5Gc-LeX |
| NJa3Ab4Gb#sp1 Neu5Gcα3Lactose |
| NJa3Ab4GNb#sp1 Neu5Gcα3LacNAc |
| NJa6Ab4GNb#sp1 Neu5Gcα6LacNAc |
| NJa6ANa#sp2 Neu5Gc6GalNAc (STn) |
| NNa#sp2 Neu5Ac |
| NNa3[6OSO3]Ab4GNb#sp2 3'Sia[6'Su]LacNAc |
| NNa3[ANb4]Ab4Gb#sp1 GM2 |
| NNa3[ANb4]Ab4GNb#sp1GM2(NAc)/CT/Sda |
| NNa3[ANb4]Ab4GNb2#sp1 sp1GM2(NAc)/CT/Sda |
| NNa3{Ab4[Fa3]GN}3b#sp1 Sia3-TriLeX |
| NNa3Ab#sp2 Neu5Acα2,3Gal |
| NNa3Ab3[6OSO3]ANa#sp2 Neu5Acα3[6Su]-T |
| NNa3Ab3[Fa4]GNb#sp2 SLe a |
| NNa3Ab3[NNa6]ANa#sp2 Di-Sia-T |
| NNa3Ab3ANa#sp2 3-Sia-T |
| NNa3Ab3GNb#sp1 Neu5Acα3Type-1 |
| NNa3Ab3GNb#sp2 Neu5Acα3Type-1 |
| NNa3Ab4[6OSO3]GNb#sp23'Sia[6Su]LacNAc |
| NNa3Ab4[Fa3][6OSO3]GNb#sp2 6Su-SLeX |
| NNa3Ab4[Fa3]GNb#sp1 SLeX |
| NNa3Ab4[Fa3]GNb#sp2 SLeX |
| NNa3Ab4[Fa3]GNb3Ab#sp2 SleX penta |
| NNa3Ab4[Fa3]GNb3Ab4GNb#sp1 SLeXLacNAc |
| NNa3Ab4Gb#sp1 3'Sialyllactose |
| NNa3Ab4Gb#sp2 3'Sialyllactose |
| NNa3Ab4GNb#sp1 3'SialyllacNAc |
| NNa3Ab4GNb#sp2 3'SialyllacNAc |
| NNa3Ab4GNb3Ab4GNb#sp1 3'SialylDiLacNAc |
| NNa3Ab4GNb3Ab4GNb3Ab4GNb#sp1 3'Sialyl-tri-LacNAc |
| NNa3ANa#sp2 Siaα3GalNAc |
| NNa6Ab#sp2 Siaα6Gal |
| NNa6Ab4[6OSO3]]GNb#sp2 6'Sial[6Su]LacNAc |
| NNa6Ab4Gb#sp1 6'Sia-lactose |
| NNa6Ab4Gb#sp2 6'Sia-lactose |
| NNa6Ab4GNb#sp1 6'Sia-LacNAc |
| NNa6Ab4GNb#sp2 6'Sia-LacNAc |
| NNa6Ab4GNb3Ab4[Fa3]GNb3Ab4[Fa3]GNb#sp1 6Sia-LacNac-LeX-LeX |
| NNa6Ab4GNb3Ab4GNb#sp1 6SiaLacNAc-LacNAc |
| NNa6ANa#sp2 6SiaβGalNAc |

TABLE 3-continued

Glycan

NNa8NNa3[ANb4]Ab4Gb#sp1 GD2
NNa8NNa3Ab4Gb#sp1 GD3
NNa8NNa8NNa3[ANb4]Ab4Gb#sp1 GT2
NNa8NNa8NNa3Ab4Gb#sp1 GT3
NNAa3[Nna6]ANa#sp2 (Sia)2-Tn
NNb#sp2 Siaβ
NNb6Ab4GNb#sp2 6'SiaβLacNAc
NNb6ANa#sp2 βSTn
OS-11#sp2 6'sialLacNAc-biantenary glycan
Ra#sp2 Rhamnose Many of the abbreviations employed in Table 3 are defined herein or at the website www.lectinity.com. In particular, the following abbreviations were used:

Sp1=OCH2CH2NH2;
Sp2=Sp3=OCH2CH2CH2NH2
A=Gal; AN=GalNAc; G=Glc; GN=GlcNAc;
F=Fucose; NN; Neu5Ac (sialic acid);
NJ=Neu5Gc (N-glycolylsialic acid); a=α; b=β;
Su=sulfo; T=Gaβ3GalNAc (T-antigen);
Tn=GalNAc (Tn-antigen); KDN=5-OH-Sia In some embodiments, glycans useful for detecting cancer include glycans of the following formula:

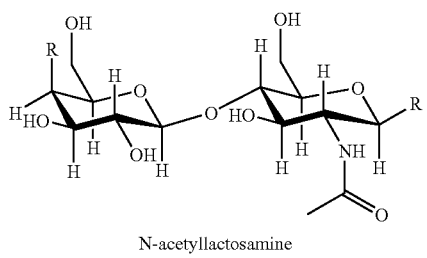

N-acetyllactosamine wherein R is a sugar residue, a disaccharide, a glycan, label or a linker.

Examples of glycans useful for detecting ovarian cancer include the following: Galβ4GlcNAcβ-R; Galβ4GlcNAcβ3Gal4GlcNAcβ-R; Galβ4GlcNAcβ3Galβ4GlcNAcβ3Galβ4GlcNAcβ-R; Fucα2Galβ4GlcNAcβ-R; Fucα2Galβ4GlcNAcβ3Galβ4GlcNAcβ-R; Fucα2Galβ4GlcNAcβ3Galβ4GlcNAcβ3Galβ4GlcNAcβ-R; GlcNAcβ3Galβ4GlcNAcβ-R; NeuAcα3Galβ4GlcNAcβ3Galβ4GlcNAcβ-R; NeuAcα3Galβ4GlcNAcβ3Galβ4GlcNAcβ3Galβ4GlcNAcβ-R; NeuAcα6Galβ4GlcNAcβ3Galβ4GlcNAcβ-R; and combinations thereof.

The glycans of the invention can have linkers, labels, linking moieties and/or other moieties attached to them. New glyco-compounds and linking systems have been described in U.S. Provisional Patent Application No. 60/833,249 filed Jul. 26, 2006. In some embodiments, glycans of the invention with linkers, labels, linking moieties and/or other moieties are identified as R groups. These linkers, labels, linking moieties and/or other moieties can be used to attach the glycans to a solid support, detect particular glycans in an assay, purify or otherwise manipulate the glycans. For example, the glycans of the invention can have amino moieties provided by attached alkylamine groups, amino acids, peptides, or proteins. In some embodiments, the glycans have alkylamine moieties such as —OCH$_2$CH$_2$NH$_2$ (called Sp1) or —OCH$_2$CH$_2$CH$_2$NH$_2$ (called Sp2 or Sp3) that have useful as linking moieties (the amine) and act as spacers or linkers.

The labels most commonly employed for these studies include radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The glycan(s) or its binding partner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{57}$Co, $^{59}$Fe, $^{90}$Y, $^{125}$I, $^{131}$I, and $^{186}$Re. Enzyme labels are likewise useful, and can be detected by any of the art-recognized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

I. Scientific Basis

Glycan Arrays for Detecting Neoplasia and Other Disorders

The invention disclosed herein addresses a need for business methods relating to preventing, detecting and/or treating neoplasia including, for example, cancer in addition to early stage disease and other disorders. In one embodiment the methods of the invention include glycan arrays. A glycan array has been described in PCT/US2005/007370 filed Mar. 7, 2005 titled "High Throughput Glycan Microarrays" and U.S. Provisional Patent Application No. 60/629,666 filed Nov. 19, 2004 titled "Development of Blood Based Test Allowing Diagnosis of Neoplasia Status", both of which are incorporated herein by this reference in their entirety and made a part of this specification.

The arrays of some embodiments of the invention employ a library of characterized and well-defined glycan structures. The array has been validated with a diverse set of carbohydrate binding proteins such as plant lectins and C-type lectins, Siglecs, Galectins, Influenza Hemaglutinins and anti-carbohydrate antibodies (both from crude sera and from purified serum fractions). Further description on how to make glycan arrays useful in the practice of the invention is provided in U.S. Provisional Ser. No. 60/550,667, filed Mar. 5, 2004, and U.S. Provisional Ser. No. 60/558,598, filed Mar. 31, 2004, the contents of which are incorporated herein by reference. In one aspect of the invention a cancer-specific array of glycan markers is provided herein. Any such array may be specific for the cancer, for instance the lung cancer array or markers provided in Tables 5 and 6 or a subset thereof, or the array may include markers for several or many cancers. Thus, markers from any one, several or all of Tables 5-13, including selected markers from one or more of the Tables 5-13, may be included in a cancer marker array.

The inventive libraries, arrays and methods have several advantages. One particular advantage of the invention is that the arrays and methods of the invention provide highly reproducible results.

Another advantage is that the libraries and arrays of some embodiments of the invention permit screening of multiple glycans in one reaction. Thus, the libraries and arrays of the invention provide large numbers and varieties of glycans. For example, the libraries and arrays of the invention have at least two, at least three, at least ten, or at least 100 glycans. In some embodiments, the libraries and arrays of the invention have about 2 to about 100,000, or about 2 to about 10,000, or about 2 to about 1,000, or about 2 to 500, or about 2 to 200, or about 2 to 100 different glycans per array. Such large numbers of glycans permit simultaneous assay of a multitude of glycan types.

Moreover, as described herein, the present arrays have been used for successfully screening a variety of glycan binding proteins. Such experiments demonstrate that little degradation of the glycan occurs and only small amounts of glycan binding proteins are consumed during a screening assay. The arrays and methods of the invention provide high signal to noise ratios. The screening methods provided by the invention are fast and easy because they involve only a few steps. In some methods, no surface modifications or blocking procedures are typically required during the assay procedures of the invention.

The composition of glycans on the arrays of the invention can be varied as needed by one of skill in the art. Many different glycoconjugates can be incorporated into the arrays of the invention including, for example, naturally occurring glycans, synthetic glycans, glycoproteins, glycopeptides, glycolipids, bacterial and plant cell wall glycans and the like. Immobilization procedures for attaching different glycans to the arrays of the invention are readily controlled to easily permit array construction.

Spacer molecules, linkers or linker/spacer groups can be used to link the glycans to the arrays. Such spacer molecules or linkers include stable (e.g. substantially chemically inert) chains or polymers. For example, the spacer molecules or linking groups can be alkylene groups. One example of an alkylene group is —(CH$_2$)n-, where n is an integer of from 1 to 10.

Unique libraries of different glycans are attached to defined regions on the solid support of the array surface by any available procedure. In general, the arrays are made by obtaining a library of glycan molecules, attaching linking moieties to the glycans in the library, obtaining a solid support that has a surface derivatized to react with the specific linking moieties present on the glycans of the library and attaching the glycan molecules to the solid support by forming a covalent linkage between the linking moieties and the derivatized surface of the solid support.

The derivatization reagent can be attached to the solid substrate via carbon-carbon bonds using, or example, substrates having (poly)trifluorochloroethylene surfaces, or more preferably, by siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups.

For example, a glycan library can be employed that has been modified to contain primary amino groups. For example, the glycans of the invention can have amino moieties provided by attached alkylamine groups, amino acids, peptides, or proteins. In some embodiments the glycans can have alkylamine groups such as the —OCH$_2$CH$_2$NH$_2$ (called Sp1) or —OCH$_2$CH$_2$CH$_2$NH$_2$ (called Sp2 or Sp3) groups attached that provide the primary amino group. The primary amino groups on the glycans can react with an N-hydroxy succinimide (NHS)-derivatized surface of the solid support. Such NHS-derivatized solid supports are commercially available. For example, NHS-activated glass slides are available from Accelr8 Technology Corporation, Denver, Colo. After attachment of all the desired glycans, slides can further be incubated with ethanolamine buffer to deactivate remaining NHS functional groups on the solid support. The array can be used without any further modification of the surface. Blocking procedures known in the art to prevent unspecific binding may be needed.

Each type of glycan is contacted or printed onto to the solid support at a defined glycan probe location. A microarray printer can be used for applying the various glycans to defined glycan probe locations. For example, about 0.1 nL to about 10 nL, or about 0.5 nL of glycan solution can be applied per defined glycan probe location. Various concentrations of the glycan solutions can be contacted or printed onto the solid support. For example, a glycan solution of about 0.1 to about 1000 micromolar glycan or about 1.0 to about 500 micromolar glycan or about 10 to about 100 micromolar glycan can be employed. In general, it may be advisable to apply each concentration to a replicate of several (for example, three to six) defined glycan probe locations. Such replicates provide internal controls that confirm the levels of binding reactions between a glycan and test molecules.

As illustrated herein, glycans that bind to antibodies in test samples from cancer patients include glycans of the following formula:

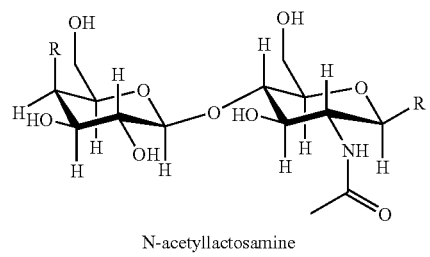

N-acetyllactosamine wherein R is a sugar residue, a disaccharide, a glycan, label or a linker.

In one exemplary embodiment the methods of the invention include glycan arrays useful in detecting, treating and/or preventing ovarian cancer. Specific examples of glycans useful for detecting ovarian cancer include the following:
Galβ4GlcNAcβ-R; Galβ4GlcNAcβ3Galβ4GlcNAcβ-R;
Galβ4GlcNAcβ3Galβ4GlcNAcβ3Galβ4GlcNAcβ-R;
Fucα2Galβ4GlcNAcβ-R;
Fucα2Galβ4GlcNAcβ3Galβ4GlcNAcβ-R;
Fucα2Galβ4GlcNAcβ3Galβ4GlcNAcβ3Galβ4GlcNAcβ-R;
GlcNAcβ3Galβ4GlcNAcβ-R;
NeuAcα3Galβ4GlcNAcβ3Galβ4GlcNAcβ-R;
NeuAcα3Galβ4GlcNAcβ3Galβ4GlcNAcβ3Galβ4GlcNAcβ-R;
NeuAcα6Galβ4GlcNAcβ3Galβ4GlcNAcβ-R; and combinations thereof, wherein R is a sugar residue, a disaccharide, a glycan, label or a linker.

Because cancer patients have antibodies that can bind with specificity to and/or discriminate these glycans and the presence of such antibodies is indicative of cancer, many of these glycans should be present on glycan arrays used for detecting cancer.

Glycopolymer Probes

The systematic study of biological processes driven by carbohydrate recognition requires multivalent carbohydrate probes. Linear polymers with pendant carbohydrates groups (Glyc; glycoside residue herein), also termed glycopolymers in this disclosure, are an exemplary practical tool for this purpose (see, e.g., N. V. Bovin in Chemical Probes in Biology; (Ed. M. P. Schneider), Kluwer Academic Publishers, The Netherlands, 2003, pp. 207-225; and N. V. Bovin, Glycoconjugate J., 1998, 15, pp. 431-446, the entire contents of which are incorporated herein by this reference and made a part of this specification).

Glycopolymer Immobilization

Libraries of polyacrylamides with various pendant carbohydrate residues and labels, for example biotin, are currently available for functional glycomics research (see Consortium for Functional Glycomics. http://glycomics.scripps.edu (accessed March 2006)). Development of bioanalytic systems and methods utilizing carbohydrate bioanalytic systems, biosensing structures and/or carbohydrate arrays need improved methods for deposition and immobilization of such glycopolymers on the surface of an array, probe, bead or the like.

U.S. Provisional Patent Application No. 60/833,249 filed Jul. 26, 2006, which is incorporated herein by reference in its entirety, describes a practical approach to synthesis of glycopolymers with end biotin groups, which are slated for introduction into a polymer scaffold during its preparation with a fragment of suitably functionalized alkylcobalt(III) chelate. The glycopolymer with biotin end group was synthesized and its high antibody binding efficacy in ELISA was demonstrated. The described polymer may be useful to construct glycoarrays and complex bio-analytical systems such as glycosylated polymer beads, liposomes and cells and the like with an engineered surface.

Glycopolymers

The glycopolymers corresponding to and of use in aspects of the invention encompass macromolecules that include at least one of the carbohydrates listed in Table 4 below, or a plurality of the carbohydrates listed in Table 4.

TABLE 4

Gala#Sp8
Glca#Sp8
Mana#Sp8
GalNAca#Sp8
Fuca#Sp8
Fuca#Sp9
Rhaa#Sp8
Neu5Aca#Sp8
Neu5Aca#Sp12
Neu5Acb#Sp8
Galb#Sp8
Glcb#Sp8
Manb#Sp8
GalNAcb#Sp8
GlcNAcb#Sp0
GlcNAcb#Sp8
GlcNGcb#Sp8
Galb1-4GlcNAcb1-3(Galb1-4GlcNAcb1-6)GalNAca#Sp8
GlcNAcb1-3(GlcNAcb1-6)GlcNAcb1-4GlcNAcb#Sp8
Gal[3OSO3,6OSO3]b1-4GlcNAc[6OSO3]b#Sp0
Gal[3OSO3,6OSO3]b1-4GlcNAcb#Sp0
Gal[3OSO3]b1-4Glcb#Sp8
Gal[3OSO3]b1-4Glc[6OSO3]b#Sp0
Gal[3OSO3]b1-4Glc[6OSO3]b#Sp8
Gal[3OSO3]b1-3(Fuca1-4)GlcNAcb#Sp8
Gal[3OSO3]b1-3GalNAca#Sp8
Gal[3OSO3]b1-3GlcNAcb#Sp8
Gal[3OSO3]b1-4(Fuca1-3)GlcNAcb#Sp8
Gal[6OSO3]b1-4GlcNAcb[6OSO3]b#Sp8
Gal[3OSO3]b1-4GlcNAcb#Sp0
Gal[3OSO3]b1-4GlcNAcb#Sp8
Gal[3OSO3]b#Sp8
Gal[4OSO3,6OSO3]b1-4GlcNAc#Sp0
Gal[4OSO3]b1-4GlcNAcb#Sp8
Man[6-H2PO3]a#Sp8
Gal[6OSO3]b1-4Glcb#Sp0
Gal[6OSO3]b1-4Glcb#Sp8
Gal[6OSO3]b1-4GlcNAcb#Sp8
Gal[6OSO3]b1-4Glc[6OSO3]b#Sp8
Neu5Aca2-3Gal[6OSO3]b1-4GlcNAcb#Sp8
GlcNAc[6OSO3]b#Sp8
Neu5Ac[9Ac]a#Sp8
Neu5Ac[9Ac]a2-6Galb1-4GlcNAcb#Sp8
Mana1-3(Mana1-6)Manb1-4GlcNAcb1-4GlcNAcb#Gly
GlcNAcb1-2Mana1-3(GlcNAcb1-2Mana1-6)Manb1-4GlcNAcb1-4GlcNAcb#Gly
Galb1-4GlcNAcb1-2Mana1-3(Galb1-4GlcNAcb1-2Mana1-6)Manb1-4GlcNAcb#Gly
Neu5Aca2-3Galb1-4GlcNAcb1-2Mana1-3(Neu5Aca2-3Galb1-4GlcNAcb1-2Mana1-6)Manb1-4GlcNAcb1-4GlcNAcb#Gly
Neu5Aca2-6Galb1-4GlcNAcb1-2Mana1-3(Neu5Aca2-6Galb1-4GlcNAcb1-2Mana1-6)Manb1-4GlcNAcb1-4GlcNAcb#Sp8
Fuca1-2Galb1-3GalNAcb1-3Gala#Sp9
Fuca1-2Galb1-3GalNAcb1-3Gala1-4Galb1-4Glcb#Sp3
Fuca1-2Galb1-3(Fuca1-4)GlcNAcb#Sp8
Fuca1-2Galb1-3GalNAca#Sp8
Fuca1-2Galb1-3GalNAcb1-4(Neu5Aca2-3)Galb1-4Glcb#Sp0
Fuca1-2Galb1-3GalNAcb1-4(Neu5Aca2-3)Galb1-4Glcb#Sp9
Fuca1-2Galb1-3GlcNAcb1-3Galb1-4Glcb#Sp10

TABLE 4-continued

Fuca1-2Galb1-3GlcNAcb1-3Galb1-4Glcb#Sp8
Fuca1-2Galb1-3GlcNAcb#Sp0
Fuca1-2Galb1-3GlcNAcb#Sp8
Fuca1-2Galb1-4(Fuca1-3)GlcNAcb1-3Galb1-4(Fuca1-3)GlcNAcb#Sp0
Fuca1-2Galb1-4(Fuca1-3)GlcNAcb1-3Galb1-4(Fuca1-3)GlcNAcb1-3Galb1-4(Fuca1-3)GlcNAcb#Sp0
Fuca1-2Galb1-4(Fuca1-3)GlcNAcb#Sp0
Fuca1-2Galb1-4(Fuca1-3)GlcNAcb#Sp8
Fuca1-2Galb1-4GlcNAcb1-3Galb1-4GlcNAcb#Sp0
Fuca1-2Galb1-4GlcNAcb1-3Galb1-4GlcNAcb1-3Galb1-4GlcNAcb#Sp0
Fuca1-2Galb1-4GlcNAcb#Sp0
Fuca1-2Galb1-4GlcNAcb#Sp8
Fuca1-2Galb1-4Glcb#Sp0
Fuca1-2Galb#Sp8
Fuca1-2????GlcNAcb#Sp8
Fuca1-3GlcNAcb#Sp8
Fuca1-4GlcNAcb#Sp8
Fucb1-3GlcNAcb#Sp8
GalNAca1-3(Fuca1-2)Galb1-3GlcNAcb#Sp0
GalNAca1-3(Fuca1-2)Galb1-4(Fuca1-3)GlcNAcb#Sp0
GalNAca1-3(Fuca1-2)Galb1-4GlcNAcb#Sp0
GalNAca1-3(Fuca1-2)Galb1-4GlcNAcb#Sp8
GalNAca1-3(Fuca1-2)Galb1-4Glcb#Sp
GalNAca1-3(Fuca1-2)Galb#Sp8
GalNAca1-3GalNAcb#Sp8
GalNAca1-3Galb#Sp8
GalNAca1-4(Fuca1-2)Galb1-4GlcNAcb#Sp8
GalNAcb1-3GalNAca#Sp8
GalNAcb1-3(Fuca1-2)Galb#Sp8
GalNAcb1-3Gala1-4Galb1-4GlcNAcb#Sp0
GalNAcb1-4(Fuca1-3)GlcNAcb#Sp0
GalNAcb1-4GlcNAcb#Sp0
GalNAcb1-4GlcNAcb#Sp8
Gala1-2Galb#Sp8
Gala1-3(Fuca1-2)Galb1-3GlcNAcb#Sp0
Gala1-3(Fuca1-2)Galb1-4(Fuca1-3)GlcNAcb#Sp0
Gala1-3(Fuca1-2)Galb1-4GlcNAcb#Sp0
Gala1-3(Fuca1-2)Galb1-4Glcb#Sp0
Gala1-3(Fuca1-2)Galb#Sp8
Gala1-3(Gala1-4)Galb1-4GlcNAcb#Sp8
Gala1-3GalNAca#Sp8
Gala1-3GalNAcb#Sp8
Gala1-3Galb1-4(Fuca1-3)GlcNAcb#Sp8
Gala1-3Galb1-3GlcNAcb#Sp0
Gala1-3Galb1-4GlcNAcb#Sp8
Gala1-3Galb1-4Glcb#Sp0
Gala1-3Galb#Sp8
Gala1-4(Fuca1-2)Galb1-4GlcNAcb#Sp8
Gala1-4Galb1-4GlcNAcb#Sp0
Gala1-4Galb1-4GlcNAcb#Sp8
Gala1-4Galb1-4Glcb#Sp0
Gala1-4GlcNAcb#Sp8
Gala1-6Glcb#Sp8
Galb1-2Galb#Sp8
Galb1-3(Fuca1-4)GlcNAcb1-3Galb1-4(Fuca1-3)GlcNAcb#Sp0
Galb1-3(Fuca1-4)GlcNAcb1-3Galb1-4GlcNAcb#Sp0
Galb1-3(Fuca1-4)GlcNAcb#Sp0
Galb1-3(Fuca1-4)GlcNAcb#Sp8
Galb1-3(Fuca1-4)GlcNAcb#Sp8
Galb1-3(Galb1-4GlcNAcb1-6)GalNAca#Sp8
Galb1-3(GlcNAcb1-6)GalNAca#Sp8
Galb1-3(Neu5Aca2-6)GalNAca#Sp8
Galb1-3(Neu5Acb2-6)GalNAca#Sp8
Galb1-3(Neu5Aca2-6)GlcNAcb1-4Galb1-4Glcb#Sp10
Galb1-3GalNAca#Sp8
Galb1-3GalNAcb#Sp8
Galb1-3GalNAcb1-3Gala1-4Galb1-4Glcb#Sp0
Galb1-3GalNAcb1-4(Neu5Aca2-3)Galb1-4Glcb#Sp0
Galb1-3GalNAcb1-4Galb1-4Glcb#Sp8
Galb1-3Galb#Sp8
Galb1-3GlcNAcb1-3Galb1-4GlcNAcb#Sp0
Galb1-3GlcNAcb1-3Galb1-4Glcb#Sp10
Galb1-3GlcNAcb#Sp0
Galb1-3GlcNAcb#Sp8
Galb1-4(Fuca1-3)GlcNAcb#Sp0
Galb1-4(Fuca1-3)GlcNAcb#Sp8
{Galb1-4(Fuca1-3)GlcNAcb1-3}2#Sp0
{Galb1-4(Fuca1-3)GlcNAcb1-3}3#Sp0
Galb1-4Glc[6OSO3]b#Sp0
Galb1-4Glc[6OSO3]b#Sp8

TABLE 4-continued

Galb1-4GalNAca1-3(Fuca1-2)Galb1-4GlcNAcb#Sp8
Galb1-4GalNAcb1-3(Fuca1-2)Galb1-4GlcNAcb#Sp8
Galb1-4GlcNAcb1-3(Galb1-4GlcNAcb1-6)GalNAca#Sp8
Galb1-4GlcNAcb1-3GalNAca#Sp8
Galb1-4GlcNAcb1-3Galb1-4(Fuca1-3)GlcNAcb1-3Galb1-4(Fuca1-3)GlcNAcb#Sp0
{Galb1-4GlcNAcb1-3}3#Sp0
Galb1-4GlcNAcb1-3Galb1-4GlcNAcb#Sp0
Galb1-4GlcNAcb1-3Galb1-4Glcb#Sp0
Galb1-4GlcNAcb1-3Galb1-4Glcb#Sp8
Galb1-4GlcNAcb1-6(Galb1-3)GalNAca#Sp8
Galb1-4GlcNAcb1-6GalNAca#Sp8
Galb1-4GlcNAcb#Sp0
Galb1-4GlcNAcb#Sp8
Galb1-4Glcb#Sp0
Galb1-4Glcb#Sp8
GlcNAcb1-3Galb1-4GlcNAcb#Sp0
GlcNAca1-6Galb1-4GlcNAcb#Sp8
GlcNAcb1-2Galb1-3GalNAca#Sp8
GlcNAcb1-3(GlcNAcb1-6)GalNAca#Sp8
GlcNAcb1-3(GlcNAcb1-6)Galb1-4GlcNAcb#Sp8
GlcNAcb1-3GalNAca#Sp8
GlcNAcb1-3Galb#Sp8
GlcNAcb1-3Galb1-3GalNAca#Sp8
GlcNAcb1-3Galb1-4GlcNAcb#Sp0
GlcNAcb1-3Galb1-4GlcNAcb#Sp8
GlcNAcb1-3Galb1-4GlcNAcb1-3Galb1-4GlcNAcb#Sp0
GlcNAcb1-3Galb1-4Glcb#Sp0
GlcNAcb1-4MDPLys (bact.cell wall)
GlcNAcb1-4(GlcNAcb1-6)GalNAca#Sp8
GlcNAcb1-4Galb1-4GlcNAcb#Sp8
GlcNAcb1-4GlcNAcb1-4GlcNAcb1-4GlcNAcb1-4GlcNAcb1-4GlcNAcb#Sp8
GlcNAcb1-4GlcNAcb1-4GlcNAcb1-4GlcNAcb1-4GlcNAcb#Sp8
GlcNAcb1-4GlcNAcb1-4GlcNAcb#Sp8
GlcNAcb1-6(Galb1-3)GalNAca#Sp8
GlcNAcb1-6GalNAca#Sp8
GlcNAcb1-6Galb1-4GlcNAcb#Sp8
Glca1-4Glcb#Sp8
Glca1-4Glca#Sp8
Glca1-6Glca1-6Glcb#Sp8
Glcb1-4Glcb#Sp8
Glcb1-6Glcb#Sp8
HOCH2(HOCH)4CH2NH2; G-ol-amine:
GlcAa#Sp8
GlcAb#Sp8
GlcAb1-3Galb#Sp8
GlcAb1-6Galb#Sp8
KDNa2-3Galb1-3GlcNAcb#Sp0
KDNa2-3Galb1-4GlcNAcb#Sp0
Mana1-2Mana1-2Mana1-3Mana#Sp9
Mana1-2Mana1-3(Mana1-2Mana1-6)Mana#Sp9
Mana1-2Mana1-3Mana#Sp9
Mana1-6(Mana1-2Mana1-3)Mana1-6(Mana1-2Mana1-3)Manb1-4GlcNAcb1-4GlcNAcb#Asn
Mana1-2Mana1-6(Mana1-3)Mana1-6(Mana1-2Mana1-2Mana1-3)Manb1-4GlcNAcb1-4GlcNAcb#Asn
Mana1-2Mana1-2Mana1-3[Mana1-2Mana1-3(Mana1-2Mana1-6)Mana1-6]Manb1-4GlcNAcb1-4GlcNAcb#Asn
Mana1-3(Mana1-6)Mana#Sp3
Mana1-3(Mana1-2Mana1-2Mana1-6)Mana#Sp9
Mana1-2Mana1-3(Mana1-3(Mana1-6)Mana1-6)Manb1-4GlcNAcb1-4GlcNAcb#Asn
Mana1-3(Mana1-3(Mana1-6)Mana1-6)Manb1-4GlcNAcb1-4GlcNAcb#Asn
Mixture of Man 5 to Man 9-Asn
Manb1-4GlcNAcb#Sp0
Neu5Aca2-3(Galb1-3GalNAcb1-4)Galb1-4Glcb#Sp0
Neu5Aca2-3Galb1-3GalNAca#Sp8
Neu5Aca2-8Neu5Aca2-8Neu5Aca2-3(GalNAcb1-4)Galb1-4Glcb#Sp0
Neu5Aca2-8Neu5Aca2-8Neu5Aca2-3(GalNAcb1-4)Galb1-4Glcb#Sp0
Neu5Aca2-8Neu5Aca2-8Neu5Aca2-3Galb1-4Glcb#Sp0
Neu5Aca2-8Neu5Aca2-3(GalNAcb1-4)Galb1-4Glcb#Sp0
Neu5Aca2-8Neu5Aca2-8Neu5Aca#Sp8
Neu5Aca2-3Gal[6OSO3]b1-4(Fuca1-3)GlcNAcb#Sp8
Neu5Aca2-3(GalNAcb1-4)Galb1-4GlcNAcb#Sp0
Neu5Aca2-3(GalNAcb1-4)Galb1-4GlcNAcb#Sp8
Neu5Aca2-3(GalNAcb1-4)Galb1-4Glcb#Sp0
Neu5Aca2-3(Neu5Aca2-3Galb1-3GalNAcb1-4)Galb1-4Glcb#Sp0
Neu5Aca2-3(Neu5Aca2-6)GalNAca#Sp8 same as 221
Neu5Aca2-3GalNAca#Sp8
Neu5Aca2-3GalNAcb1-4GlcNAcb#Sp0
Neu5Aca2-3Gal[6OSO3]b1-3GlcNAc#Sp8
Neu5Aca2-3Galb1-3(Fuca1-4)GlcNAcb#Sp8
Neu5Aca2-3Galb1-3(Fuca1-4)GlcNAcb1-3Galb1-4(Fuca1-3)GlcNAcb#Sp0
Neu5Aca2-3Galb1-3(Neu5Aca2-3Galb1-4)GlcNAcb#Sp8

TABLE 4-continued

Neu5Aca2-3Galb1-3GalNAc[6OSO3]a#Sp8
Neu5Aca2-3(Neu5Aca2-6)GalNAca#Sp8
Neu5Aca2-3Galb#Sp8
Neu5Aca2-3Galb1-3GalNAcb1-3Galb1-4Galb1-4Glcb#Sp0
Neu5Aca2-3Galb1-3GalNAcb1-3Galb1-4GlcNAcb#Sp0
Neu5Aca2-3Galb1-3GlcNAcb#Sp0
Neu5Aca2-3Galb1-3GlcNAcb#Sp8
Neu5Aca2-3Galb1-4GlcNAc[6OSO3]b#Sp8
Neu5Aca2-3Galb1-4(Fuca1-3)GlcNAc[6OSO3]b#Sp8
Neu5Aca2-3Galb1-4(Fuca1-3)GlcNAcb1-3Galb1-4(Fuca1-3)GlcNAcb1-3Galb1-4(Fuca1-3)GlcNAcb#Sp0
Neu5Aca2-3Galb1-4(Fuca1-3)GlcNAcb#Sp0
Neu5Aca2-3Galb1-4(Fuca1-3)GlcNAcb#Sp8
Neu5Aca2-3Galb1-4(Fuca1-3)GlcNAcb1-3Galb#Sp8
Neu5Aca2-3Galb1-4(Fuca1-3)GlcNAcb1-3Galb1-4GlcNAcb#Sp8
Neu5Aca2-3Galb1-4GlcNAcb1-3Galb1-4(Fuca1-3)GlcNAc#Sp0
Neu5Aca2-3Galb1-4GlcNAcb1-3Galb1-4GlcNAcb1-3Galb1-4GlcNAcb#Sp0
Neu5Aca2-3Galb1-4GlcNAcb#Sp0
Neu5Aca2-3Galb1-4GlcNAcb#Sp8
Neu5Aca2-3Galb1-4GlcNAcb1-3Galb1-4GlcNAcb#Sp0
Neu5Aca2-3Galb1-4Glcb#Sp0
Neu5Aca2-3Galb1-4Glcb#Sp8
Neu5Aca2-6(Galb1-3)GalNAca#Sp8
Neu5Aca2-6GalNAca#Sp8
Neu5Aca2-6GalNAcb1-4GlcNAcb#Sp0
Neu5Aca2-6Galb1-4GlcNAc[6OSO3]b#Sp8
Neu5Aca2-6Galb1-4GlcNAcb#Sp0
Neu5Aca2-6Galb1-4GlcNAcb#Sp8
Neu5Aca2-6Galb1-4GlcNAcb1-3Galb1-4(Fuca1-3)GlcNAcb1-3Galb1-4(Fuca1-3)GlcNAcb#Sp0
Neu5Aca2-6Galb1-4GlcNAcb1-3Galb1-4GlcNAcb#Sp0
Neu5Aca2-6Galb1-4Glcb#Sp0
Neu5Aca2-6Galb1-4Glcb#Sp8
Neu5Aca2-6Galb#Sp8
Neu5Aca2-8Neu5Aca#Sp8
Neu5Aca2-8Neu5Aca2-3Galb1-4Glcb#Sp0
Neu5Acb2-6GalNAca#Sp8
Neu5Acb2-6Galb1-4GlcNAcb#Sp8
Neu5Acb2-6(Galb1-3)GalNAca#Sp8
Neu5Gca2-3Galb1-3(Fuca1-4)GlcNAcb#Sp0
Neu5Gca2-3Galb1-3GlcNAcb#Sp0
Neu5Gca2-3Galb1-4(Fuca1-3)GlcNAcb#Sp0
Neu5Gca2-3Galb1-4GlcNAcb#Sp0
Neu5Gca2-3Galb1-4Glcb#Sp0
Neu5Gca2-6GalNAca#Sp0
Neu5Gca2-6Galb1-4GlcNAcb#Sp0
Neu5Gca#Sp8

The glycopolymers alternatively can comprise at least one macromolecule listed in Tables 1-3 and other tables in PCT/US2005/007370 filed Mar. 7, 2005 titled "High Throughput Glycan Microarrays"; and U.S. Provisional Patent Application No. 60/629,666 filed Nov. 19, 2004 titled "Development of Blood Based Test Allowing Diagnosis of Neoplasia Status". In one aspect, the glycopolymers are cancer-associated glycopolymers. In a particular such aspect, the glycopolymers comprise one or more macromolecule listed in Tables 5-13.

In another embodiment, any conjugate from a group identified above is provided with an additional fluorescent label which can be bound to the conjugate as is known in the art. The fluorescent label is used in methods for quantitative control of immobilization and evaluation of the substance amount in a solution.

In another embodiment, any conjugate from a group identified above included at least two different residues of oligosaccharide and/or a combination oligosaccharide/noncarbohydrate. i.e., complex epitopes.

Neoplasia

As discussed herein, in one aspect the invention relates to, for example, diagnostic screening of risk of neoplasia or cancer, the existence of neoplasia or cancer in a patient or the monitoring of treatment associated with neoplasia or cancer. Neoplasia is generally defined as abnormal, disorganized growth in a tissue or organ. Such a growth can be in the form of a mass, often called a neoplasm, tumor or cancer. Neoplasms can be benign or malignant lesions. Malignant lesions are often called cancer. The National Institute of Health lists thirteen cancers as the most frequently diagnosed in the United States, each having an estimated annual incidence for 2006 at 30,000 cases or more. These most frequently diagnosed cancers include: bladder cancer, melanoma, breast cancer, non-Hodgkin's lymphoma, colon and rectal cancer, pancreatic cancer, endometrial cancer, prostate cancer, kidney (renal cell) cancer, skin cancer (non-melanoma), leukemia, thyroid cancer and lung cancer. Source: cancer.gov/cancertopics/commoncancers. Last accessed Sep. 12, 2006.

An extensive listing of cancer types includes but is not limited to acute lymphoblastic leukemia (adult), acute lymphoblastic leukemia (childhood), acute myeloid leukemia (adult), acute myeloid leukemia (childhood), adrenocortical carcinoma, adrenocortical carcinoma (childhood), AIDS-related cancers, AIDS-related lymphoma, anal cancer, astrocytoma (childhood cerebellar), astrocytoma (childhood cerebral), basal cell carcinoma, bile duct cancer (extrahepatic), bladder cancer, bladder cancer (childhood), bone cancer (osteosarcoma/malignant fibrous histiocytoma), brain stem glioma (childhood), brain tumor (adult), brain tumor—brain stem glioma (childhood), brain tumor—cerebellar astrocytoma (childhood), brain tumor—cerebral astrocytoma/malignant glioma (childhood), brain tumor—ependymoma (childhood), brain tumor—medulloblastoma (childhood), brain tumor—supratentorial primitive neuroectodermal tumors (childhood), brain tumor—visual pathway and hypothalamic glioma (childhood), breast cancer (female, male, childhood), bronchial adenomas/carcinoids (childhood), Burkitt's lymphoma, carcinoid tumor (childhood), carcinoid tumor (gastrointestinal), carcinoma of unknown primary site (adult and childhood), central nervous system lymphoma (primary), cerebellar astrocytoma (childhood), cerebral astrocytoma/malignant glioma (childhood), cervical cancer, chronic lymphocytic leukemia, chronic myelogenous leukemia, chronic myeloproliferative disorders, colon cancer, colorectal cancer (childhood), cutaneous t-cell lymphoma, endometrial cancer, ependymoma (childhood), esophageal cancer, esophageal cancer (childhood), Ewing's family of tumors, extracranial germ cell tumor (childhood), extragonadal germ cell tumor, extrahepatic bile duct cancer, eye cancer (intraocular melanoma and retinoblastoma), gallbladder cancer, gastric (stomach) cancer, gastric (stomach) cancer (childhood), gastrointestinal carcinoid tumor, gastrointestinal stromal tumor (gist), germ cell tumor (extracranial (childhood), extragonadal, ovarian), gestational trophoblastic tumor, glioma (adult), glioma (childhood: brain stem, cerebral astrocytoma, visual pathway and hypothalamic), hairy cell leukemia, head and neck cancer, hepatocellular (liver) cancer (adult primary and childhood primary), Hodgkin's lymphoma (adult and childhood), Hodgkin's lymphoma during pregnancy, hypopharyngeal cancer, hypothalamic and visual pathway glioma (childhood), intraocular melanoma, islet cell carcinoma (endocrine pancreas), Kaposi's sarcoma, kidney (renal cell) cancer, kidney cancer (childhood), laryngeal cancer, laryngeal cancer (childhood), leukemia—acute lymphoblastic (adult and childhood), leukemia, acute myeloid (adult and childhood), leukemia—chronic lymphocytic, leukemia—chronic myelogenous, leukemia—hairy cell, lip and oral cavity cancer, liver cancer (adult primary and childhood primary), lung cancer—non-small cell, lung cancer—small cell, lymphoma—AIDS—related, lymphoma—Burkitt's, lymphoma—cutaneous t-cell, lymphoma—Hodgkin's (adult, childhood and during pregnancy), lymphoma—non-Hodgkin's (adult, childhood and during pregnancy), lymphoma—primary central nervous system, macroglobulinemia—Waldenström's, malignant fibrous histiocytoma of bone/osteosarcoma, medulloblastoma (childhood), melanoma, melanoma—intraocular (eye), Merkel cell carcinoma, mesothelioma (adult) malignant, mesothelioma (childhood), metastatic squamous neck cancer with occult primary, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia, chronic, myeloid leukemia (adult and childhood) acute, myeloma—multiple, myeloproliferative disorders—chronic, nasal cavity and paranasal sinus cancer, nasopharyngeal cancer, nasopharyngeal cancer (childhood), neuroblastoma, non-small cell lung cancer, oral cancer (childhood), oral cavity and lip cancer, oropharyngeal cancer, osteosarcoma/malignant fibrous histiocytoma of bone, ovarian cancer (childhood), ovarian epithelial cancer, ovarian germ cell tumor, ovarian low malignant potential tumor, pancreatic cancer, pancreatic cancer (childhood), pancreatic cancer—islet cell, paranasal sinus and nasal cavity cancer, parathyroid cancer, penile cancer, pheochromocytoma, pineoblastoma and supratentorial primitive neuroectodermal tumors (childhood), pituitary tumor, plasma cell neoplasm/multiple myeloma, pleuropulmonary blastoma, pregnancy and breast cancer, primary central nervous system lymphoma, prostate cancer, rectal cancer, renal cell (kidney) cancer, renal cell (kidney) cancer (childhood), renal pelvis and ureter—transitional cell cancer, retinoblastoma, rhabdomyosarcoma (childhood), salivary gland cancer, salivary gland cancer (childhood), sarcoma—Ewing's family of tumors, sarcoma—Kaposi's, sarcoma—soft tissue (adult and childhood), sarcoma—uterine, Sézary syndrome, skin cancer (non-melanoma), skin cancer (childhood), skin cancer (melanoma), skin carcinoma—Merkel cell, small cell lung cancer, small intestine cancer, soft tissue sarcoma (adult and childhood), squamous cell carcinoma, squamous neck cancer with occult primary—metastatic, stomach (gastric) cancer, stomach (gastric) cancer (childhood), supratentorial primitive neuroectodermal tumors (childhood), testicular cancer, thymoma (childhood), thymoma and thymic carcinoma, thyroid cancer, thyroid cancer (childhood), transitional cell cancer of the renal pelvis and ureter, trophoblastic tumor, gestational, ureter and renal pelvis—transitional cell cancer, urethral cancer, uterine cancer—endometrial, uterine sarcoma, vaginal cancer, visual pathway and hypothalamic glioma (childhood), vulvar cancer, Waldenström's macroglobulinemia, and Wilms' tumor. Source: cancer.gov/cancertopics/alphalist. Last accessed Sep. 12, 2006.

Accordingly, the present glycan libraries, glycan arrays and methods for detecting, monitoring and treating neoplasia are very useful because various embodiments of the invention can be used to in conjunction with a host of neoplasms. One form of cancer, ovarian cancer, is discussed below and provided merely as exemplary description of one cancer application. The below discussion of ovarian cancer, as descriptive, is not intended to limit or restrict any aspect of the invention.

Ovarian Cancer

Ovarian cancer is the most lethal of gynecological malignancies with a mortality rate of 60%. The five-year survival rates for the various clinical stages of the disease are as follows: Stage I>90%, Stage II=80%, Stage III=20% and Stage IV=10%; there is a significant drop in the survival rates at later stages of the disease. Standard-of-care treatment for advanced stages of the disease includes cytoreductive surgery followed by chemotherapy.

For most patients there is a low probability of surviving, since approximately 75% of all patients are diagnosed at stages III and IV of the disease, and poor prognosis is associated with late diagnosis of the disease at its advanced stages. Resistance to currently-available chemotherapeutic agents is another major problem. Although complete clinical response is achieved in 75% of patients after initial treatment, most will develop recurrent disease and require re-treatment. Unfortunately, the overwhelming majority will eventually develop chemoresistance and succumb to the disease.

Accordingly, the present glycan libraries, glycan arrays and methods for detecting and monitoring ovarian cancer are particularly useful because they can be used to detect ovarian cancer, for example, in the early stages of the disease, thereby increasing survival rates. As noted above, the present glycan libraries, glycan arrays and methods for detecting and monitoring cancer are particularly useful because they can be used to detect cancer, for example, in the early stages of the disease, thereby increasing survival rates. The libraries, arrays and methods herein may be utilized in detection and/or monitoring of cancer, including lung cancer, breast cancer, and ovarian cancer. Particular glycan markers for each of lung cancer, breast cancer, and ovarian cancer are set out herein, including in Tables 5-13.

Methods of Detecting Cancer

According to the invention, cancer patients have circulating antibodies that bind with specificity to specific types of glycans. Healthy persons who do not have cancer have much lower levels of such antibodies, or substantially no antibodies that react with such glycans.

Thus, in one embodiment, the invention provides methods for detecting and diagnosing cancer in a patient. In particular embodiments, methods for detecting and diagnosing lung cancer, breast cancer, and ovarian cancer in a patient are provided. The method involves contacting a test sample from a patient with a library or array of glycans and observing whether antibodies in the test sample bind to selected glycans. The pattern of glycans bound by antibodies from cancer patients can be compared to the pattern of glycans bound by antibodies in serum samples from healthy, non-cancerous patients. Glycans to which antibodies in the test sample may bind include glycans of the following formula:

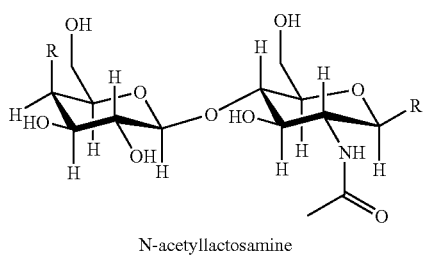

N-acetyllactosamine wherein R is a sugar residue, a disaccharide, a glycan, label or a linker.

Specific examples of glycans useful for detecting cancer include the following: Galβ4GlcNAcβ-R; Galβ4GlcNAcβ3Galβ4GlcNAcβ-R; Galβ4GlcNAcβ3Galβ4GlcNAcβ3Galβ4GlcNAcβ-R; Fucα2Galβ4GlcNAcβ-R; Fucα2Galβ4GlcNAcβ3Galβ4GlcNAcβ-R; Fucα2Galβ4GlcNAcβ3Galβ4GlcNAcβ3Galβ4GlcNAcβ-R; GlcNAcβ3Galβ4GlcNAcβ-R; NeuAcα3Galβ4GlcNAcβ3Galβ4GlcNAcβ-R; NeuAcα3Galβ4GlcNAcβ3Galβ4GlcNAcβ3Galβ4GlcNAcβ-R; NeuAcα6Galβ4GlcNAcβ3Galβ4GlcNAcβ-R; and combinations thereof, wherein R is a sugar residue, a disaccharide, a glycan, label or a linker.

For detecting cancer, a test sample is obtained from a patient. The patient may or may not have cancer. In this case, the methods of the invention are used to diagnose or detect whether the patient has cancer, or a particular type of cancer, or has a propensity for developing cancer, or a particular type of cancer. Alternatively, the methods of the invention can be used with patients that are known to have cancer, or a particular type of cancer. In this case, the prognosis of cancer, or a particular type of cancer, can be monitored. Complementary such approaches are utilized for any of various specific cancers, including ovarian cancer, breast cancer, lung cancer, etc. such as and including as described further below and herein.

With regard to disease or cancer for assessment, the test sample obtained from the patient can be any tissue, pathology or bodily fluid sample. For example, the test sample can be is a blood sample, a serum sample, a plasma sample, a urine sample, a cervical secretion sample, a vaginal secretion sample, an ovarian fluid or tissue sample, an ascites fluid sample, a plural ascites fluid sample, a saliva sample, a cerebrospinal fluid sample, or a tissue sample. In many embodiments, the sample is a serum sample.

Detection of binding can be direct, for example, by detection of a label attached to a molecule that binds to antibodies or other proteins or polypeptides. Detection can be indirect, for example, by detecting a labeled secondary antibody that can bind to human antibodies. The bound label can be observed using any available detection method. For example, an array scanner can be employed to detect fluorescently labeled molecules that are bound to array. In experiments illustrated herein a ScanArray 5000 (GSI Lumonics, Watertown, Mass.) confocal scanner was used. The data from such an array scanner can be analyzed by methods available in the art, for example, by using ImaGene image analysis software (BioDiscovery Inc., El Segundo, Calif.).

In general, as illustrated herein, detection of increased glycan binding by antibodies (or other binding entities) in a patient's serum is an indicator that the patient may have cancer, including as described herein ovarian cancer, breast cancer, lung cancer. Comparison of the levels of glycan binding over time provides an indication of whether the cancer is progressing toward metastasis, whether a patient is responding to a selected treatment or whether the cancer is in remission. Hence, the invention also provides methods for monitoring the progression of cancer in a patient.

Further description of methods for detecting molecules that bind to glycan arrays is provided in U.S. Provisional Ser. No. 60/550,667, filed Mar. 5, 2004, and U.S. Provisional Ser. No. 60/558,598, filed Mar. 31, 2004, the contents of which are incorporated herein by reference.

Methods of Treating Cancer

Conventional treatments for cancer have been focused on the treatment of a later stage disease and include removal of the diseased organ, localized removal of the tumor, radiation, and chemotherapy. While these techniques are often effective, they suffer from certain deficiencies. Removal of the diseased organ may provide the best assurance against local recurrence of the cancer, but may have unfortunate effects upon the physiology of the patient, such as for instance, in the instance of removal of the ovaries, the reproductive future of the patient and upon the hormonal balance of the patient. Therefore, the decision to remove the diseased organ requires the patient to make difficult choices. Removal of just the tumorous tissues is less disfiguring, but is associated with greater risk of recurrence of the cancer. Radiation and chemotherapy are arduous and are not completely effective against recurrence. Such conventional treatments therefore have drawbacks.

As described above, the invention provides methods for early detection of precancerous and cancerous conditions. In another embodiment, the invention provides compositions for preventing and treating cancer. Such compositions include one or more glycans that are typically recognized by circulating antibodies present in patients with cancer, or a particular type of cancer. Glycans that can be included in the compositions of the invention include glycans of the following formula:

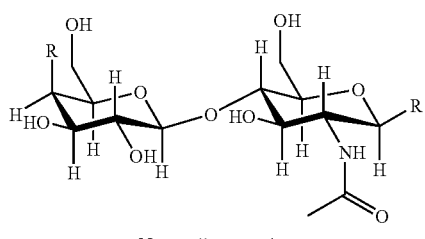

N-acetyllactosamine wherein R is a sugar residue, a disaccharide, a glycan, label or a linker.

Specific examples of glycans useful for detecting cancer include the following: Galβ4GlcNAcβ-R; Galβ4GlcNAcβ3Galβ4GlcNAcβ-R; Galβ4GlcNAcβ3Galβ4GlcNAcβ3Galβ4GlcNAcβ-R; Fucα2Galβ4GlcNAcβ-R; Fucα2Galβ4GlcNAcβ3Galβ4GlcNAcβ-R; Fucα2Galβ4GlcNAcβ3Galβ4GlcNAcβ3Galβ4GlcNAcβ-R; GlcNAcβ3Galβ4GlcNAcβ-R; NeuAcα3Galβ4GlcNAcβ3Galβ4GlcNAcβ-R; NeuAcα3Galβ4GlcNAcβ3Galβ4GlcNAcβ3Galβ4GlcNAcβ-R; NeuAcα3Galβ4GlcNAcβ3Galβ4GlcNAcβ-R; and combinations thereof, wherein R is a sugar residue, a disaccharide, a glycan, label or a linker. Particular glycans for detection, diagnosis and/or monitoring of lung cancer, breast cancer, and ovarian cancer, are provided in Tables 5-6, 7-10, and 11-13, respectively.

One of skill in the art may choose to use the glycan without a spacer or linker (e.g. without SP1 or SP2) when preparing the glycan compositions of the invention.

A further aspect of the invention provides a method of treating cancer, the method comprising administering to the patient an effective amount of a composition that includes glycans identified in autoantibody-glycan binding interactions in screening serum samples of cancer patients. In some embodiments, the type and amount of glycan is effective to provoke an anti-cancer cell immune response in the patient.

The anti-cancer compositions of the invention may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. The composition can be administered with an adjuvant or with immune-stimulating cytokines, such as interleukin-2. An example of an immune-stimulating adjuvant is Detox. The glycans may also be conjugated to a suitable carrier such as keyhole limpet haemocyanin (KLH) or mannan (see WO 95/18145 and Longenecker et al (1993) Ann. NY Acad. Sci. 690, 276-291). The glycans can be administered to the patient orally, intramuscularly or intradermally or subcutaneously.

In some embodiments, the compositions of the invention are administered in a manner that produces a humoral response. Thus, production of antibodies directed against the glycan(s) is one measure of whether a successful immune response has been achieved.

In other embodiments, the compositions of the invention are administered in a manner that produces a cellular immune response, resulting in tumor cell killing by NK cells or cytotoxic T cells (CTLs). Strategies of administration, which activate T helper cells are particularly useful. As described above, it may also be useful to stimulate a humoral response. It may be useful to co-administer certain cytokines to promote such a response, for example interleukin-2, interleukin-12, interleukin-6, or interleukin-10.

It may also be useful to target the immune compositions to specific cell populations, for example antigen presenting cells, either by the site of injection, by use delivery systems, or by selective purification of such a cell population from the patient and ex vivo administration of the glycan(s) to such antigen presenting cells. For example, dendritic cells may be sorted as described in Zhou et al (1995) Blood 86, 3295-3301; Roth et al (1996) Scand. J. Immunology 43, 646-651.

A further aspect of the invention therefore provides a vaccine effective against cancer, or against cancer or tumor cells, comprising an effective amount of glycans that are bound by circulating antibodies of cancer patients.

Antibodies Relating to the Invention

The invention provides antibodies that bind to glycans that react with circulating antibodies present in cancer patients. Such antibodies are useful for the diagnosis, monitoring and treatment of cancer. As is illustrated herein, different patients may have produced different amounts and somewhat different types of antibodies against the cancer-associated glycan epitopes of the invention. Hence, administration of antibodies that are known to have good affinity for the cancer-associated glycan epitopes of the invention will be beneficial even though the patient has begun to produce some antibodies reactive with cancer epitopes. Thus, the invention provides antibody preparations that can bind the cancer associated glycan epitopes described herein.

Antibodies can be prepared using a selected glycan, class of glycans or mixture of glycans as the immunizing antigen. The glycan or glycan mixture can be coupled to a carrier protein, if desired. Such commonly used carrier proteins, which are chemically coupled to epitopes include keyhole limpet hemocyanin (KLH), thyroglobulin, bovine serum albumin (BSA), and tetanus toxin. A coupled protein can be used to immunize the animal (e.g., a mouse, a rat, or a rabbit).

If desired, polyclonal or monoclonal antibodies can be further purified, for example, by binding to and elution from a matrix to which the glycan or mixture of glycans to which the antibodies were raised is bound. Those of skill in the art will know of various techniques common in the immunology arts for purification and/or concentration of polyclonal antibodies, as well as monoclonal antibodies (Coligan, et al., Unit 9, Current Protocols in Immunology, Wiley Interscience, 1991, incorporated by reference).

It is also possible to use the anti-idiotype technology to produce monoclonal antibodies, which mimic an epitope. For example, an anti-idiotypic monoclonal antibody made to a first monoclonal antibody will have a binding domain in the hypervariable region, which is the "image" of the epitope bound by the first monoclonal antibody.

An antibody suitable for binding to a glycan is specific for at least one portion or region of the glycan. For example, one of skill in the art can use a whole glycan or fragment of glycan to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art (Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference). For example, a glycan or glycan mixture is injected into an animal host, preferably according to a predetermined schedule incorporating one or more booster immunizations, and the animal is bled periodically. Polyclonal antibodies specific for a glycan or glycan fragment may then be purified from such antisera by, for example, affinity chromatography using the glycan coupled to a suitable solid support.

The preparation of monoclonal antibodies likewise is conventional (Kohler & Milstein, *Nature*, 256:495 (1975); Coligan et al., sections 2.5.1-2.6.7; and Harlow et al., Antibodies: A Laboratory Manual, page 726 (Cold Spring Harbor Pub. 1988)), which are hereby incorporated by reference. Briefly, monoclonal antibodies can be obtained by injecting mice with a composition comprising an antigen (glycan), verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of monoclonal antibodies are available to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large-scale hybridoma cultivation can be carried out by homogenous suspension culture in an air reactor, in a continuous stirrer reactor, or immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristine tetramethylpentadecane prior to injection. After one to three weeks, the desired monoclonal antibody is recovered from the body fluid of the animal.

Antibodies can also be prepared through use of phage display techniques. In one example, an organism is immunized with an antigen, such as a glycan or mixture of glycans of the invention. Lymphocytes are isolated from the spleen of the immunized organism. Total RNA is isolated from the splenocytes and mRNA contained within the total RNA is reverse transcribed into complementary deoxyribonucleic acid (cDNA). The cDNA encoding the variable regions of the light and heavy chains of the immunoglobulin is amplified by polymerase chain reaction (PCR). To generate a single chain fragment variable (scFv) antibody, the light and heavy chain amplification products may be linked by splice overlap extension PCR to generate a complete sequence and ligated into a suitable vector. E. coli are then transformed with the vector encoding the scFv, and are infected with helper phage, to produce phage particles that display the antibody on their surface. Alternatively, to generate a complete antigen binding fragment (Fab), the heavy chain amplification product can be fused with a nucleic acid sequence encoding a phage coat protein, and the light chain amplification product can be cloned into a suitable vector. E. coli expressing the heavy chain fused to a phage coat protein are transformed with the vector encoding the light chain amplification product. The disulfide linkage between the light and heavy chains is established in the periplasm of E. coli. The result of this procedure is to produce an antibody library with up to $10^9$ clones. The size of the library can be increased to $10^{18}$ phage by later addition of the immune responses of additional immunized organisms that may be from the same or different hosts. Antibodies that recognize a specific antigen can be selected through panning. Briefly, an entire antibody library can be exposed to an immobilized antigen against which antibodies are desired. Phage that do not express an antibody that binds to the antigen are washed away. Phage that express the desired antibodies are immobilized on the antigen. These phage are then eluted and again amplified in E. coli. This process can be repeated to enrich the population of phage that express antibodies that specifically bind to the antigen. After phage are isolated that express an antibody that binds to an antigen, a vector containing the coding sequences for the antibody can be isolated from the phage particles and the coding sequences can be re-cloned into a suitable vector to produce an antibody in soluble form. In another example, a human phage library can be used to select for antibodies, such as monoclonal antibodies, that bind to ovarian cancer specific glycan epitopes. Briefly, splenocytes may be isolated from a human that has ovarian cancer and used to create a human phage library according to methods as described above and known in the art. These methods may be used to obtain human monoclonal antibodies that bind to the ovarian cancer specific glycan epitopes. Phage display methods to isolate antigens and antibodies are known in the art and have been described (Gram et al., Proc. Natl. Acad. Sci., 89:3576 (1992); Kay et al., Phage display of peptides and proteins: A laboratory manual. San Diego: Academic Press (1996); Kermani et al., Hybrid, 14:323 (1995); Schmitz et al., Placenta, 21 Suppl. A:S106 (2000); Sanna et al., Proc. Natl. Acad. Sci., 92:6439 (1995)).

An antibody of the invention may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described (Orlandi et al., Proc. Nat'l Acad. Sci. USA, 86:3833 (1989) which is hereby incorporated in its entirety by reference). Techniques for producing humanized monoclonal antibodies are described (Jones et al., Nature, 321:522 (1986); Riechmann et al., Nature, 332:323 (1988); Verhoeyen et al, Science, 239:1534 (1988); Carter et al., Proc. Nat'l Acad. Sci. USA, 89:4285 (1992); Sandhu, Crit. Rev. Biotech., 12:437 (1992); and Singer et al., J. Immunol., 150:2844 (1993), which are hereby incorporated by reference).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens (e.g. the glycans described herein), and the mice can be used to produce human antibody-secreting hybridomas. Methods for obtaining human antibodies from transgenic mice are described (Green et al., Nature Genet., 7:13 (1994); Lonberg et al., Nature, 368:856 (1994); and Taylor et al., Int. Immunol., 6:579 (1994), which are hereby incorporated by reference).

Antibody fragments of the invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described (U.S. Pat. Nos. 4,036,945; 4,331,647; and 6,342,221, and references contained therein; Porter, *Biochem. J.,* 73:119 (1959); Edelman et al., Methods in Enzymology, Vol. 1, page 422 (Academic Press 1967); and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments include an association of $V_H$ and $V_L$ chains. This association may be noncovalent (Inbar et al., *Proc. Nat'l Acad. Sci. USA,* 69:2659 (1972)). Alternatively, the variable chains can be linked by an intermolecular disulfide bond or cross-linked by chemicals such as glutaraldehyde (Sandhu, *Crit. Rev. Biotech.,* 12:437 (1992)). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli.* The recombinant host cells synthesize a single polypeptide chain with a linker peptide bridging the two V domains. Methods for producing sFvs are described (Whitlow et al., Methods: A Companion to Methods in Enzymology, Vol. 2, page 97 (1991); Bird et al., *Science,* 242:423 (1988), Ladner et al., U.S. Pat. No. 4,946,778; Pack et al., *Bio/Technology,* 11:1271 (1993); and Sandhu, *Crit. Rev. Biotech.,* 12:437 (1992)).

Another form of an antibody fragment is a peptide that forms a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., Methods: A Companion to Methods in Enzymology, Vol. 2, page 106 (1991)).

An antibody of the invention may be coupled to a toxin. Such antibodies may be used to treat animals, including humans that suffer from ovarian cancer. For example, an antibody that binds to a glycan that is etiologically linked to development of ovarian cancer may be coupled to a tetanus toxin and administered to a patient suffering from ovarian cancer. The toxin-coupled antibody can bind to a ovarian cancer cell and kill it.

An antibody of the invention may be coupled to a detectable tag. Such antibodies may be used within diagnostic assays to determine if an animal, such as a human, has ovarian cancer. Examples of detectable tags include, fluorescent proteins (i.e., green fluorescent protein, red fluorescent protein, yellow fluorescent protein), fluorescent markers (i.e., fluorescein isothiocyanate, rhodamine, texas red), radiolabels (i.e., $^3$H, $^{32}$P, $^{125}$I) enzymes (i.e., â-galactosidase, horseradish peroxidase, â-glucuronidase, alkaline phosphatase), or an affinity tag (i.e., avidin, biotin, streptavidin). Methods to couple antibodies to a detectable tag are known in the art. Harlow et al., Antibodies: A Laboratory Manual, page 319 (Cold Spring Harbor Pub. 1988).

Dosages, Formulations and Routes of Administration

The compositions of the invention are administered so as to achieve an immune response against a glycan bound by antibodies typically present in the serum of patients with neoplasia or other disorders. In some embodiments, the compositions of the invention are administered so as to achieve a reduction in at least one symptom associated with a neoplasia (e.g., ovarian cancer, breast cancer, lung cancer) or other disorder.

To achieve the desired effect(s), the glycan or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, what types of glycans are administered, the route of administration, the progression or lack of progression of the cancer, the weight, the physical condition, the health, the age of the patient, whether prevention or treatment is to be achieved, and if the glycan is chemically modified. Such factors can be readily determined by the clinician employing animal models or other test systems that are available in the art.

Administration of the therapeutic agents (glycans) in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the glycans or combinations thereof may be essentially continuous over a pre-selected period of time or may be in a series of spaced doses. Both local and systemic administration is contemplated.

To prepare the composition, the glycans or antibodies or combinations thereof are synthesized or otherwise obtained, and purified as necessary or desired. These therapeutic agents can then be lyophilized or stabilized, their concentrations can be adjusted to an appropriate amount, and the therapeutic agents can optionally be combined with other agents. The absolute weight of a given glycan, binding entity, antibody or combination thereof that is included in a unit dose can vary widely. For example, about 0.01 to about 2 g, or about 0.1 to about 500 mg, of at least one glycan, binding entity, or antibody specific for a particular glycan can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the glycan(s), binding entities, antibodies or combinations thereof can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste. Orally administered therapeutic agents of the invention can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic agents of the invention can be prepared by procedures known in the art using well-known and readily available ingredients. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the therapeutic agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, C1-C4 alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and â-tocopherol and its derivatives can be added.

Additionally, the therapeutic agents are well suited to formulation as sustained release dosage forms and the like. The formulations can be so constituted that they release the active agent, for example, in a particular part of the vascular system or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

In general, such dosage forms comprise an amount of at least one of the agents of the invention effective to treat or prevent the clinical symptoms of ovarian cancer. Any statistically significant attenuation of one or more symptoms of ovarian cancer is considered to be a treatment of ovarian cancer.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 im, alternatively between 2 and 3 im. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular immune response, vascular condition or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, other anti-cancer agents and the like, whether for the conditions described or some other condition.

Kits

The present invention further pertains to a packaged pharmaceutical or diagnostic composition such as a kit for detecting, controlling, preventing or treating a neoplasia (e.g., ovarian cancer, breast cancer, lung cancer) or other disorder. In one exemplary embodiment, the kit or container holds an array or library of glycans for detecting cancer and instructions for using the array or library of glycans for detecting the cancer. The array includes at least one glycan that is bound by antibodies present in serum samples of a cancer patient.

In another embodiment, the kit or container holds a therapeutically effective amount of a pharmaceutical composition for controlling cancer and instructions for using the pharmaceutical composition for control of the cancer. The pharmaceutical composition includes at least one glycan of the present invention, in a therapeutically effective amount such that the cancer is controlled, prevented or treated.

In a further embodiment, the kit comprises a container containing an antibody that specifically binds to a glycan that is associated with cancer or metastatic cancer. The antibody can have a directly attached or indirectly associated therapeutic agent. The antibody can also be provided in liquid form, powder form or other form permitting ready administration to a patient.

The kits of the invention can also comprise containers with tools useful for administering the compositions of the invention. Such tools include syringes, swabs, catheters, antiseptic solutions and the like.

As described herein and shown in FIG. 1, in certain embodiments a kit 201 can include a housing or container 203 for housing various components. As shown in FIG. 1, and described herein, the kit 201 can optionally include libraries and/or arrays of glycans 205, instructions 209 and reagents 207. Other embodiments of the kit 201 are envisioned wherein the components include various additional features described herein.

Data Analysis/Review/Transmission

In another embodiment, a result obtained using the methods described herein is used for detection/treatment/prevention of early stage diseases and/or neoplasia of an individual, for example, a patient. In a further embodiment, the method of detection/treatment/prevention of early stage diseases and/or neoplasia includes reviewing or analyzing data relating to the presence of, for example, circulating antibodies that react with cancer-related epitopes in a sample. A conclusion is then provided to a patient, a health care provider or a health care manager, the conclusion being based on the review or analysis of data regarding a disease diagnosis or early stage disease detection. It is envisioned that in another embodiment that providing a conclusion to a patient, a health care provider or a health care manager includes transmission of the data over a network.

Figure 2:
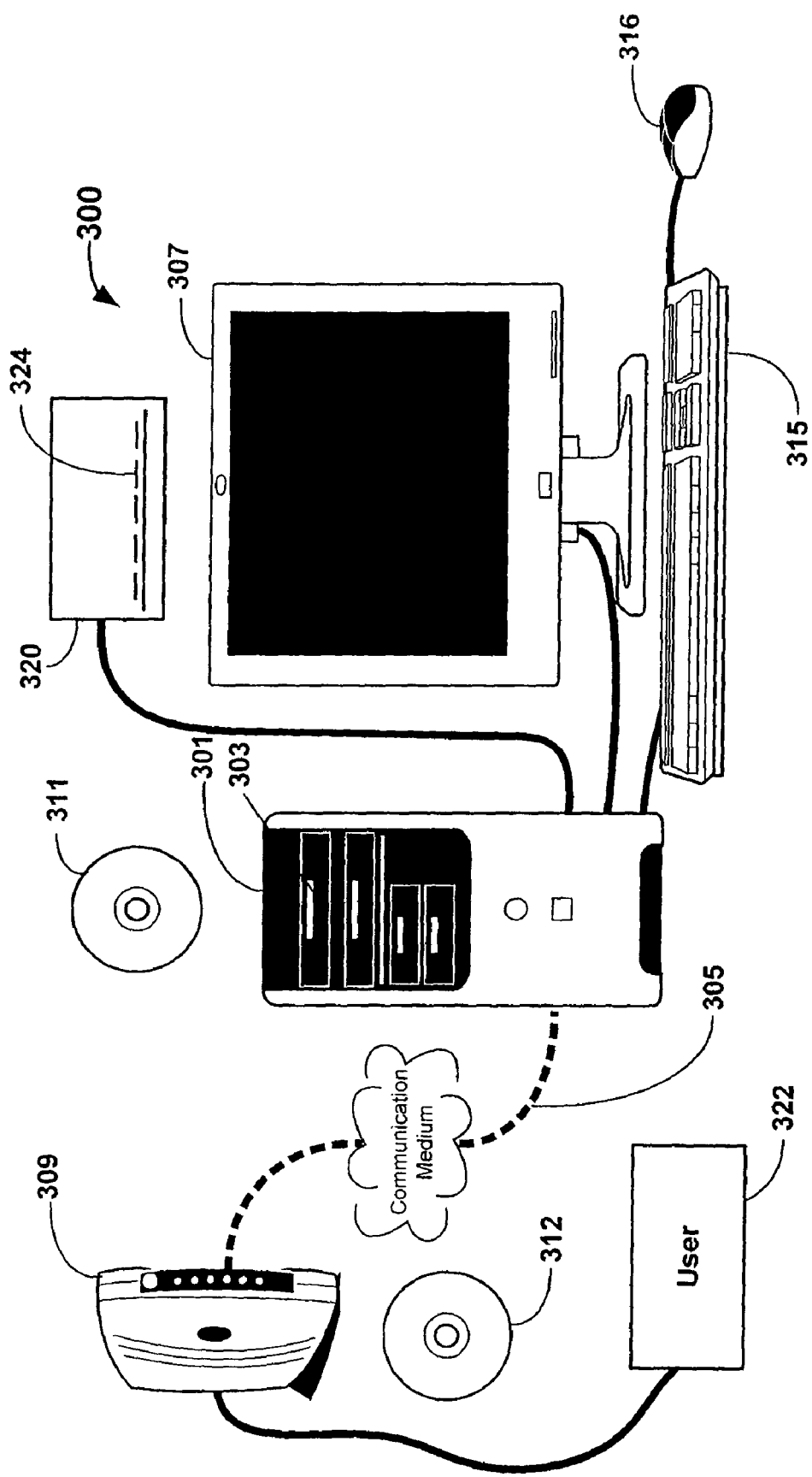
FIG. 2 is a block diagram showing a representative example logic device in communication with an apparatus for use with the invention.

FIG. 2 is a block diagram showing a representative example logic device through which reviewing or analyzing data relating to the present invention can be achieved. Such data can be in relation to detection/treatment/prevention of early stage diseases and/or neoplasia in an individual. FIG. 2 shows a computer system (or digital device) 300 connected to an apparatus 320 for use with libraries and arrays of glycans 324 to, for example, produce a result. The computer system 300 may be understood as a logical apparatus that can read instructions from media 311 and/or network port 305, which can optionally be connected to server 309 having fixed media 312. The system shown in FIG. 2 includes CPU 301, disk drives 303, optional input devices such as keyboard 315 and/or mouse 316 and optional monitor 307. Data communication can be achieved through the indicated communication medium to a server 309 at a local or a remote location. The communication medium can include any means of transmitting and/or receiving data. For example, the communication medium can be a network connection, a wireless connection or an internet connection. Such a connection provide for communication over the World Wide Web. It is envisioned that data relating to the present invention can be transmitted over such networks or connections for reception and/or review by a party 322. The receiving party 322 can be a patient, a health care provider or a health care manager.

In one embodiment, a computer-readable medium includes a medium suitable for transmission of a result of an analysis of a biological sample. The medium can include a result regarding detection/treatment/prevention of early stage diseases and/or neoplasia of a subject, wherein such a result is derived using the methods described herein.

Exemplary Syntheses, Isolations, Preparations, Uses and Diagnoses

Examples of enzymatic synthesis of glycans, synthesis of sialic-acid-containing oligosaccharides, synthesis of ganglioside mimics, isolation of glycans from natural sources, preparations, and use of glycan arrays, and diagnosis of breast neoplasia and ovarian cancer using glycan arrays are disclosed in Ser. No. 60/747,272 U.S. Provisional Patent Application, filed May 15, 2006, the entire contents of which are incorporated herein by this reference and made a part of this specification.

The glycan-binding moieties of the invention can be in the form of any of a number of moieties. In one embodiment the glycan-binding moieties can be a protein, polypeptide, antibody, enzyme, nucleic acid, cell and/or a pathogen.

Patient test samples can include biological or other samples taken from one or more individuals. The individuals can be healthy individuals or those with known or suspected disease. Test samples can include but are not limited to blood, sera or other bodily fluids, even respiration. In a particular embodiment greater than 100 patient test samples are screened. In one embodiment greater than 1,000 patient test samples are screened. In another embodiment the patient test samples are obtained from academic or non-profit organizations. In yet another embodiment the patient test samples are obtained from profit-based organizations In one embodiment, screening a patient test sample includes using an array of glycan molecules. The array of glycan molecules can include solid support and an arrayed library of glycan molecules. In use, the array of glycan molecules as disclosed herein can be used in a screening process with a patient test sample to detect binding between glycan-binding moieties and the arrayed glycan molecules.

In another embodiment, a diagnostic product can be identified using the screening methods described herein. It is further envisioned that a diagnostic product could include a second array of glycan molecules including a plurality of the identified diagnostic markers. In this embodiment the diagnostic product can include a collection of two or more identified diagnostic markers useful as a diagnostic product for one or more condition or disorder in a patient.

In one embodiment, screening patient test samples can include screening a plurality of glycan molecules carried by at least one solid support. It is envisioned that the solid support can include arrays, beads, microspheres, plates, slides and/or probes.

It is further envisioned that screening patient test samples can include screening a plurality of glycan molecules carried within a microfluidic system.

In another embodiment, wherein a diagnostic product that is identified is a diagnostic marker, such a diagnostic marker can include a plurality of diagnostic markers.

The arrayed library of glycan molecules can be configured in any of a number of different ways. In one embodiment the glycan molecules include N-acetyllactosamin-containing glycans. In another embodiment greater than about 10 glycan molecules are arrayed on a solid support. In a further embodiment greater than about 200 glycan molecules are arrayed. In yet another embodiment about 1,000 glycan molecules are arrayed.

The method includes identifying at least one glycan capable of reacting with antibodies associated with neoplasia in sera or bodily fluids of a subject having benign, pre-malignant or malignant neoplasia. In a further step, the method includes preparing at least one administrable composition comprising a carrier and one or more of the at least one glycan for use as vaccine products directed toward the neoplasia.

It is envisioned that the targeted neoplasia can include any of a number of neoplasms including but not limited to cancers. In one embodiment the neoplasia is selected from the group including ovarian cancer, breast cancer, cervical cancer, bladder cancer, melanoma, non-Hodgkin's lymphoma, colon and rectal cancer, pancreatic cancer, endometrial cancer, prostate cancer, kidney cancer, skin cancer, leukemia, thyroid cancer and lung cancer. In particular embodiments the neoplasia is selected from lung cancer, breast cancer, and ovarian cancer.

Other cancers include but are not limited to: acute lymphoblastic leukemia (adult), acute lymphoblastic leukemia (childhood), acute myeloid leukemia (adult), acute myeloid leukemia (childhood), adrenocortical carcinoma, adrenocortical carcinoma (childhood), AIDS-related cancers, AIDS-related lymphoma, anal cancer, astrocytoma (childhood cerebellar), astrocytoma (childhood cerebral), basal cell carcinoma, bile duct cancer (extrahepatic), bladder cancer, bladder cancer (childhood), bone cancer (osteosarcoma/malignant fibrous histiocytoma), brain stem glioma (childhood), brain tumor (adult), brain tumor—brain stem glioma (childhood), brain tumor—cerebellar astrocytoma (childhood), brain tumor—cerebral astrocytoma/malignant glioma (childhood), brain tumor—ependymoma (childhood), brain tumor—medulloblastoma (childhood), brain tumor—supratentorial primitive neuroectodermal tumors (childhood), brain tumor—visual pathway and hypothalamic glioma (childhood), breast cancer (female, male, childhood), bronchial adenomas/carcinoids (childhood), Burkitt's lymphoma, carcinoid tumor (childhood), carcinoid tumor (gastrointestinal), carcinoma of unknown primary site (adult and childhood), central nervous system lymphoma (primary), cerebellar astrocytoma (childhood), cerebral astrocytoma/malignant glioma (childhood), cervical cancer, chronic lymphocytic leukemia, chronic myelogenous leukemia, chronic myeloproliferative disorders, colon cancer, colorectal cancer (childhood), cutaneous t-cell lymphoma, endometrial cancer, ependymoma (childhood), esophageal cancer, esophageal cancer (childhood), Ewing's family of tumors, extracranial germ cell tumor (childhood), extragonadal germ cell tumor, extrahepatic bile duct cancer, eye cancer (intraocular melanoma and retinoblastoma), gallbladder cancer, gastric (stomach) cancer, gastric (stomach) cancer (childhood), gastrointestinal carcinoid tumor, gastrointestinal stromal tumor (gist), germ cell tumor (extracranial (childhood), extragonadal, ovarian), gestational trophoblastic tumor, glioma (adult), glioma (childhood: brain stem, cerebral astrocytoma, visual pathway and hypothalamic), hairy cell leukemia, head and neck cancer, hepatocellular (liver) cancer (adult primary and childhood primary), Hodgkin's lymphoma (adult and childhood), Hodgkin's lymphoma during pregnancy, hypopharyngeal cancer, hypothalamic and visual pathway glioma (childhood), intraocular melanoma, islet cell carcinoma (endocrine pancreas), Kaposi's sarcoma, kidney (renal cell) cancer, kidney cancer (childhood), laryngeal cancer, laryngeal cancer (childhood), leukemia—acute lymphoblastic (adult and childhood), leukemia, acute myeloid (adult and childhood), leukemia—chronic lymphocytic, leukemia—chronic myelogenous, leukemia—hairy cell, lip and oral cavity cancer, liver cancer (adult primary and childhood primary), lung cancer—non-small cell, lung cancer—small cell, lymphoma—AIDS-related, lymphoma—Burkitt's, lymphoma—cutaneous t-cell, lymphoma—Hodgkin's (adult, childhood and during pregnancy), lymphoma—non-Hodgkin's (adult, childhood and during pregnancy), lymphoma—primary central nervous system, macroglobulinemia—Waldenström's, malignant fibrous histiocytoma of bone/osteosarcoma, medulloblastoma (childhood), melanoma, melanoma—intraocular (eye), Merkel cell carcinoma, mesothelioma (adult) malignant, mesothelioma (childhood), metastatic squamous neck cancer with occult primary, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia, chronic, myeloid leukemia (adult and childhood) acute, myeloma-multiple, myeloproliferative disorders—chronic, nasal cavity and paranasal sinus cancer, nasopharyngeal cancer, nasopharyngeal cancer (childhood), neuroblastoma, non-small cell lung cancer, oral cancer (childhood), oral cavity and lip cancer, oropharyngeal cancer, osteosarcoma/malignant fibrous histiocytoma of bone, ovarian cancer (childhood), ovarian epithelial cancer, ovarian germ cell tumor, ovarian low malignant potential tumor, pancreatic cancer, pancreatic cancer (childhood), pancreatic cancer—islet cell, paranasal sinus and nasal cavity cancer, parathyroid cancer, penile cancer, pheochromocytoma, pineoblastoma and supratentorial primitive neuroectodermal tumors (childhood), pituitary tumor, plasma cell neoplasm/multiple myeloma, pleuropulmonary blastoma, pregnancy and breast cancer, primary central nervous system lymphoma, prostate cancer, rectal cancer, renal cell (kidney) cancer, renal cell (kidney) cancer (childhood), renal pelvis and ureter—transitional cell cancer, retinoblastoma, rhabdomyosarcoma (childhood), salivary gland cancer, salivary gland cancer (childhood), sarcoma—Ewing's family of tumors, sarcoma—Kaposi's, sarcoma—soft tissue (adult and childhood), sarcoma—uterine, Sézary syndrome, skin cancer (non-melanoma), skin cancer (childhood), skin cancer (melanoma), skin carcinoma—Merkel cell, small cell lung cancer, small intestine cancer, soft tissue sarcoma (adult and childhood), squamous cell carcinoma, squamous neck cancer with occult primary—metastatic, stomach (gastric) cancer, stomach (gastric) cancer (childhood), supratentorial primitive neuroectodermal tumors (childhood), testicular cancer, thymoma (childhood), thymoma and thymic carcinoma, thyroid cancer, thyroid cancer (childhood), transitional cell cancer of the renal pelvis and ureter, trophoblastic tumor, gestational, ureter and renal pelvis—transitional cell cancer, urethral cancer, uterine cancer-endometrial, uterine sarcoma, vaginal cancer, visual pathway and hypothalamic glioma (childhood), vulvar cancer, Waldenström's macroglobulinemia, and Wilms' tumor.

In another embodiment the products can include one or more cytokines for co-administration with the administrable vaccine (administrable composition). Cytokines include but are not limited to interleukins (e.g., IL-1, IL-2, IL-3, IL-4, IL-5, IL-6, IL-7, IL-8, IL-9, IL-10, IL-11, IL-12, etc.) and interferons (e.g., IFN-α, IFN-β, IFN-γ). It is envisioned that other growth factors might be useful for co-administration with the administrable vaccine of the invention. Such growth factors include but are not limited to PDGF, EGF, TGF-α, FGF, NGF, Erythropoietin, TGF-β, IGF-I and IGF-II.

It is envisioned that antibodies associated with neoplasia and thus relevant to the invention and methods described herein, can originate from either humoral or cellular immune responses. Accordingly, in one embodiment the antibodies originate from a humoral immune response associated with neoplasia. In a particular embodiment the antibodies originate from a humoral immune response associated with, for example, ovarian cancer, breast cancer, cervical cancer, bladder cancer, melanoma, non-Hodgkin's lymphoma, colon and rectal cancer, pancreatic cancer, endometrial cancer, prostate cancer, kidney cancer, skin cancer, leukemia, thyroid cancer and lung cancer. In another embodiment the antibodies originate from cellular immune response associated with neoplasia selected from the group consisting of ovarian cancer, breast cancer, cervical cancer, bladder cancer, melanoma, non-Hodgkin's lymphoma, colon and rectal cancer, pancreatic cancer, endometrial cancer, prostate cancer, kidney cancer, skin cancer, leukemia, thyroid cancer and lung cancer.

In general, in another aspect of the invention, it is contemplated that the cancer- or disease-relevant oligosaccharides or glycans may be isolated, generated, synthesized, or manufactured as compositions. This aspect of the invention includes screening mammalian or non-mammalian sources for glycosyltransferase activity. After screening, genes encoding glycosyltransferase activity are isolated and cloned to identify one or more products for producing oligosaccharides. After identifying the products for producing oligosaccharides, they can be collaboratively or independently, marketed or commercialized. In practicing the methods of the present invention, many conventional techniques in molecular biology, for example gene cloning, are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5th Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990), all of which are incorporated herein by reference.

In another aspect, the invention includes identifying and isolating antibodies capable of reacting with circulating antibodies associated with neoplasia present in subjects or patients having a neoplasia. The circulating antibodies are subject or patient antibodies that can bind neoplasia-associated glycan epitopes. The isolated reactive antibodies are screened to identify one or more diagnostic, therapeutic or imaging antibodies, which are suitable as probes or imaging agents, such as in in vitro or in vivo applications.

The invention contemplates and includes identifying and isolating antibodies capable of reacting with circulating antibodies in a patient having, for example, lung cancer, breast cancer, or ovarian cancer. It is envisioned that reactive antibody products can be thereby generated for use in diagnostics or therapeutics In another embodiment the reactive antibodies are generated by immunization of animals or using phage display. Additionally, it is envisioned that the reactive antibodies comprise antibodies selected from the group consisting of monoclonal antibodies, polyclonal antibodies, humanized antibodies and antibody fragments.

The invention includes determining the three-dimensional structure of antigenic epitopes associated with tumor associated carbohydrate antigens (TACAs). A further step includes designing and producing monoclonal antibody fragments reactive with the epitopes for use as diagnostic, therapeutic or imaging probe products and compositions.

In a particular embodiment the three-dimensional structure TACA epitopes are determined using x-ray crystallography or NMR imaging. It is envisioned that other protein structure determination methods could be used for establishing the three-dimensional structure of TACA epitopes, including but not limited to circular dichroism and cryo-electron microscopy.

The glycan markers identified herein provide targets for disease intervention or therapy, either alone, in combination one or more with another, or in combination with other anti-cancer therapies. Thus, the glycan markers provide a glycomics-related target. The glycomics-related target is licensed for a consideration. A glycomics-related target can include but is not limited to a glycan, a glycan-binding moiety, a vaccine, a gene encoding glycosyltransferase activity, a reactive antibody and a monoclonal antibody cocktail.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Neoplasia Related Glycan Signatures

A glycan array has been utilized to identify anti-glycan autoantibody signatures which comprise a glycan marker or a plurality of glycan markers that can constitute a signature of a neoplasia or cancer. A glycan array can be of the type described in PCT/US2005/007370 filed Mar. 7, 2005 titled "High Throughput Glycan Microarrays", U.S. Provisional Patent Application No. 60/629,666 filed Nov. 19, 2004 titled "Development of Blood Based Test Allowing Diagnosis of Neoplasia Status", and U.S. Provisional Ser. No. 60/550,667, filed Mar. 5, 2004, and U.S. Provisional Ser. No. 60/558,598, filed Mar. 31, 2004.

In the field of lung cancer, an exemplary test evaluated a total of 49 patients with a history of smoking and compared the anti-glycan autoantibody profiles with that of a total of 41 adenocarcinoma patients. Adenocarcinoma of the lung is the most common type of lung cancer, and accounts for over 30% of all cases of lung cancer. Such adenocarcinoma arises from the secretory (glandular) cells located in the epithelial lining of the bronchi. Adenocarcinomas tend to be slow-growing, and spread of tumors can occur through the lymphatic vessels to lymph nodes located within the lung, mediastinum and thorax. If spread by the blood stream, tumors often can develop in the liver, the opposite lung, bones and the brain. Cigarette smoking is the main predisposing factor for adenocarcimomas. Also, it has been recognised that passive smoking can also put people at risk. A test method that would allow early for detection of adenocarcinoma, in particular a test that could discriminate adenocarcinomas against a background of patients with a history of smoking could have significant value in allowing early intervention.

In Table 5 below, a cluster of 4 glycans are identified that provide a power of discrimination in the field of lung carcinomas, and when used in a combination as is known in the art can provide a substantial power of discrimination. In the left column of Table 5, ID numbers are listed for convenience. In one method of the invention, a measurement is made of at least one antiglycan autoantibody binding profile of a test sample such as serum, and then the measured profile is compared with a profile of a normal patient or the profile of a patient with a history of smoking. In this method, a substantial difference in the test sample profile versus the normal profile or the smoking history profile can be indicative of adenocarcinoma. In one method, the measuring step comprises measuring antiglycan autoantibody binding profiles against at least two glycans selected from the group of glycans of Table 5.

TABLE 5

| ID | Glycan structures |
|---|---|
| LC-1 | Gal[3OSO3]β1-3(Fucα1-4)GlcNAcβ-sp |
| LC-2 | Neu5Acα2-3(6-O-Su)Galβ1-4(Fucα1-3)GlcNAcβ-sp |
| LC-3 | Galβ1-3Galβ-sp |
| LC-4 | Galβ1-4GlcNAcβ1-6(GlcNAcβ1-3)Galβ1-4GlcNAcβ-sp2 |

In Table 6 below, a cluster of 9 glycans are identified which includes the subset of LCs 1-4 that are listed in Table 5. In the same trial of 49 patients with a history of smoking and 41 adenocarcinoma patients referred to above, it was found that the expanded cluster of 9 glycans can provide a substantial power of discrimination.

TABLE 6

| Glycan ID | Glycan structures |
|---|---|
| LC-1 | Gal[3OSO3]β1-3(Fucα1-4)GlcNAcβ-sp |
| LC-2 | Neu5Acα2-3(6-O-Su)Galβ1-4(Fucα1-3)GlcNAcβ-sp |
| LC-3 | Galβ1-3Galβ-sp |
| LC-4 | Galβ1-4GlcNAcβ1-6(GlcNAcβ1-3)Galβ1-4GlcNAcβ-sp2 |
| LC-5 | (Glcα1-6)4β-sp4 (isomaltotetraose) |
| LC-6 | Neu5Acα2-3Galβ1-4-(6-Su)GlcNAcβ-sp |
| LC-7 | 4'-Su-Galβ1-4GlcNAcβ-sp |
| LC-8 | Galα1-3(Galα1-4)Galβ1-4GlcNAcβ-sp |
| LC-9 | Neu5Acα2-8Neu5Acα2-3Galβ1-4Glcβ-sp4 |

In the field of breast cancer, patients with DCIS and IDC were independently evaluated by anti-glycan antibody profiling. A trial was conducted with a glycan array of serum test samples of 20 patients with DCIS (ductal carcinoma in situ) which was compared to serum test samples from 20 normal patients. DCIS is biologically different and less dangerous than invasive breast cancer, but it early detection would be important for monitoring patients. A DCIS lesion is a collection of cancer cells inside the branching milk ducts of the breast, where 90 percent of breast cancers form. The cancer is termed "in situ" because the cells haven't escaped beyond the walls of the milk ducts to invade other tissues, or metastasize to other parts of the body. In Table 7 below, a cluster of 3 glycans are identified that provide a power of discrimination in the field of breast cancer. In one method of the invention, a patient can be diagnosed, or a diagnosis facilitated, of DCIS by obtaining a test sample from a patient and detecting the presence of antiglycan autoantibodies against at least one of, or a combination of, the glycans listed in Table 7.

TABLE 7

| ID | Glycan Structure |
|---|---|
| BC-1 | Galα1-4GlcNAcβ1-3Galβ1-4GlcNAcβ-sp |
| BC-2 | Neu5Acα2-3Galβ1-3GalNAcα-sp |
| BC-3 | 3'-O-Su-LacNAcβ-sp2 |

In Table 8 below, a cluster of 10 glycans are identified which includes the subset of BC-1, BC-2 and BC-3 that are listed in Table 7. In the same trial of DCIS patients referred to above, it was found that the expanded cluster of 10 glycans can provide a substantial power of discrimination. In one method of the invention, a patient can be diagnosed, or a diagnosis facilitated, of DCIS by obtaining a test sample from a patient and detecting the presence of antiglycan autoantibodies against at least one of, or a combination of, the glycans listed in Table 8.

TABLE 8

| ID | Glycan Structure |
|---|---|
| BC-1 | Galα1-4GlcNAcβ1-3Galβ1-4GlcNAcβ-sp |
| BC-2 | Neu5Acα2-3Galβ1-3GalNAcα-sp |
| BC-3 | 3'-O-Su-LacNAcβ-sp2 |
| BC-4 | 3'-O-Su-Lacβ-sp2 |
| BC-5 | Manβ1-4GlcNAcβ-sp4 |
| BC-6 | Galβ1-3Galβ-sp |
| BC-7 | (Neu5Acα2-8)3β-sp |
| BC-8 | 3',6,6'-O-Su3-LacNAcβ-sp2 (as di-sodium salt) |
| BC-9 | GAlβ1-3(Fucα1-4)GlcNAcβ-sp |
| BC-10 | 3'-O-Su-LacNAcβ-sp |

In the test of DCIS versus normal test samples described above, the precision was determined to be 82.5%, the sensitivity was 85% and the specificity was 80%.

In breast cancer, a trial was conducted with a glycan array of serum test samples of 20 patients with IDC which was compared to serum test samples from 20 normal patients. In Table 9 below, a cluster of 2 glycans are identified that provide a power of discrimination in the field of breast cancer. In one method of the invention, a patient can be diagnosed, or a diagnosis facilitated, of IDC by obtaining a test sample from a patient and detecting the presence of antiglycan autoantibodies against at least one of, or a combination of, the glycans listed in Table 9.

TABLE 9

| ID | Glycan Structure |
|---|---|
| BC-11 | Manβ1-4GlcNAcβ-sp4 |
| BC-12 | Galα1-4GlcNAcβ1-3Galβ1-4GlcNAcβ-sp |

In Table 10 below, a cluster of 10 glycans are identified which includes the subset of BC-11 and BC-12 that are listed in Table 10. In the same trial of IDC patients referred to above, it was found that the expanded cluster of 10 glycans can provide a substantial power of discrimination. In one method of the invention, a patient can be diagnosed, or a diagnosis facilitated, of IDC by obtaining a test sample from a patient and detecting the presence of antiglycan autoantibodies against at least one of, or a combination of, the glycans listed in Table 10.

TABLE 10

| ID | Glycan Structure |
|---|---|
| BC-11 | Manβ1-4GlcNAcβ-sp4 |
| BC-12 | Galα1-4GlcNAcβ1-3Galβ1-4GlcNAcβ-sp |
| BC-13 | Galβ1-3Galβ1-4GlcNAcβ-sp4 |
| BC-14 | Fucα1-3GlcNAcβ-sp |
| BC-15 | Glcβ1-6Glcβ-sp4 |
| BC-16 | Galα1-3GalNAcα-sp |
| BC-17 | GlcNAcβ1-3(Fucα1-4)GlcNAcβ-sp |
| BC-18 | GlcAβ1-3Galβ-sp |
| BC-19 | Galβ1-3GalNAcβ-sp |
| BC-20 | |

In the test of IDC versus normal test samples described above, the precision was determined to be 82.5%, the sensitivity was 75% and the specificity was 90%.

In Table 11 below, a cluster of 4 glycans are identified that were found to provide a power of discrimination in the field of ovarian cancer. A trial was conducted with a glycan array of serum test samples of 21 patients with early stage, high grade ovarian cancer which was compared to serum test samples from 145 control patients. In one method of the invention, a patient can be diagnosed, or a diagnosis facilitated, of early stage ovarian cancer by obtaining a test sample from a patient and detecting the presence of antiglycan autoantibodies against at least one of, or a combination of, the glycans listed in Table 11.

TABLE 11

| ID | Glycan Structure |
|---|---|
| OV-1 | Galβ1-4GlcNAcβ1-6GalNAcα-sp |
| OV-2 | Galβ1-4GlcNAcβ1-6GalNAcα-sp |
| OV-3 | GlcNAcβ1-3(GlcNAcβ1-6)Galβ1-4GlcNAcβ-sp2 |
| OV-4 | 3',6-O-Su2-LacNAcβ-sp (as sodium salt) |

In Table 12 below, a cluster of 10 glycans are identified which includes the subset of OV-1 through OV-4 that are listed in Table 11. In the same trial of ovarian cancer referred to above, it was found that the expanded cluster of 10 glycans can provide a substantial power of discrimination. In one method of the invention, a patient can be diagnosed, or a diagnosis facilitated, of early stage ovarian cancer by obtaining a test sample from a patient and detecting the presence of antiglycan autoantibodies against at least one of, or a combination of, the glycans listed in Table 8. In this ovarian test, the precision was determined to be 69.9%, the sensitivity was 66.7% and the specificity was 70.3%.

TABLE 12

| ID | Glycan Structure |
|---|---|
| OV-1 | Galβ1-4GlcNAcβ1-6GalNAcα-sp |
| OV-2 | Galβ1-4GlcNAcβ1-6GalNAcα-sp |
| OV-3 | GlcNAcβ1-3(GlcNAcβ1-6)Galβ1-4GlcNAcβ-sp2 |
| OV-4 | 3',6-O-Su2-LacNAcβ-sp (as sodium salt) |
| OV-5 | 6,6'-O-Su2-Lacβ-sp2 |
| OV-6 | 3',4'-O-Su2-LacNAcβ-sp (as sodium salt) |
| OV-7 | 6'-HSO3LacNAcβ-sp |
| OV-8 | 3',6,6'-O-Su3-LacNAcβ-sp2 (as di-sodium salt) |
| OV-9 | Neu5Acα2-8Neu5Acα-OCH2C6H4-p-sp4 |
| OV-10 | GlcNAcβ-sp |

The following additional glycans were identified in analyses using an expanded control set of 192 patients, as set out in Table 13. It is noteworthy that the OV-12 structure corresponds to OV-11 with an additional spacer.

TABLE 13

| ID | Glycan Structure |
|---|---|
| OV-11 | Neu5Acα2-3Galβ1-4-(6-Su)-GlcNAcβ-sp |
| OV-12 | 6'-HSO3LacNAcβ-sp2 |

The above data is analyzed to determine whether there are core oligosaccharide structures found in one or more glycan markers and/or across more than one cancer group. Further, additional, including related or extended glycan structures can be generated and/or the glycans modified or derivatized and further assessed by the methods described herein to evaluate aspects of and structural motifs in the glycan epitopes. The above data indicates that altered antiglycan binding to or against sulfated (sialo) lactosamines may be measured or detected in the various cancers. The sulfated (sialo) lactosamines include, in general, any or one or more of a family of molecules having a general sulfated lactosamine core structure [3S and/or 6S]Galβ1-4GalcNAc[3S and/or 6S], including with or without sulfation, fucosylation and core extension at the reducing end. Altered binding to one or more members of such family of sulfated (sialo) lactosamines can be associated with the presence of cancer in a patient.

A glycan array has been utilized to identify anti-glycan autoantibody signatures which comprise a glycan marker or a plurality of glycan markers that can constitute a signature of a neoplasia or cancer. In Table 14 below, a cluster of 5 glycans are identified that were found to provide a power of discrimination in the field of mesothelioma. A trial was conducted with a glycan array of serum test samples of 69 patients with mesothelioma which was compared to serum test samples from 69 control patients who have been exposed to asbestos. In one method of the invention, a patient can be diagnosed, or a diagnosis facilitated, of mesothelioma by obtaining a test sample from a patient and detecting the presence of antiglycan autoantibodies against at least one of, or a combination of, the glycans listed in Table 14.

TABLE 14

| ID | Glycan Structure |
|---|---|
| Meso-1 | Neu5Acα2-3Galβ1-4Glcβ-sp4 |
| Meso-2 | 6-O-Su-Lacβ-sp2 |
| Meso-3 | GlcNAcβ1-4(GlcNAcβ1-6)GalNAcα-sp |
| Meso-4 | Galβ1-4GlcNAcβ1-6GalNAcα-sp |
| Meso-5 | (Neu5Acα2-8)3β-sp |

In Table 15 below, a cluster of 10 glycans are identified which includes the subset of Meso-1 through Meso-5 that are listed in Table 14. In the same trial of mesothelioma referred to above, it was found that the expanded cluster of 10 glycans can provide a substantial power of discrimination. In one method of the invention, a patient can be diagnosed, or a diagnosis facilitated, of mesothelioma by obtaining a test sample from a patient and detecting the presence of antiglycan autoantibodies against at least one of, or a combination of, the glycans listed in Table 15. In this mesothelioma test, the precision was determined to be 73.7%, the sensitivity was 71% and the specificity was 76.5%.

TABLE 15

| ID | Glycan Structure |
|---|---|
| Meso-1 | Neu5Acα2-3Galβ1-4Glcβ-sp4 |
| Meso-2 | 6-O-Su-Lacβ-sp2 |
| Meso-3 | GlcNAcβ1-4(GlcNAcβ1-6)GalNAcα-sp |
| Meso-4 | Galβ1-4GlcNAcβ1-6GalNAcα-sp |
| Meso-5 | (Neu5Acα2-8)3β-sp |
| Meso-6 | GlcNAcβ1-3Galβ1-4Glcβ-sp2 |
| Meso-7 | GlcNAcβ1-6GalNAcα-sp |
| Meso-8 | Galβ1-3(Neu5Acβ2-6)GalNAcα-sp |
| Meso-9 | Galα1-4GlcNAcβ1-3Galβ1-4GlcNAcβ-sp |
| Meso-10 | Galβ1-4(6-O-Su)GlcNAcβ-sp |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for diagnosing a patient for lung cancer comprising obtaining a test sample from a patient and detecting the presence of antiglycan autoantibodies:
    (a) against at least two cell surface glycans selected from the group listed in LC-1, LC-2, LC-3 and LC-4;
    (b) against a combination of the glycans listed in LC-1, LC-2, LC-3 and LC-4; or
    (c) against a combination of the glycans listed in LC-1, LC-2, LC-3, LC-4, LC-5, LC-6, LC-7, LC-8 and LC-9.

2. The method of claim 1 wherein adenocarcinoma of the lung is diagnosed.

* * * * *